US009990863B2

(12) United States Patent
Chiribiri et al.

(10) Patent No.: US 9,990,863 B2
(45) Date of Patent: Jun. 5, 2018

(54) PERFUSION PHANTOM DEVICE

(71) Applicant: KING'S COLLEGE LONDON, London (GB)

(72) Inventors: Amedeo Chiribiri, London (GB); Eike Nagel, London (GB); Niloufar Zarinabad Nooralipour, London (GB); Roman Wesolowski, London (GB)

(73) Assignee: King's College London, London (GB)

( * ) Notice: Subject to any disclaimer, the term of this patent is extended or adjusted under 35 U.S.C. 154(b) by 81 days.

(21) Appl. No.: 14/774,506

(22) PCT Filed: Mar. 10, 2014

(86) PCT No.: PCT/GB2014/050705
§ 371 (c)(1),
(2) Date: Sep. 10, 2015

(87) PCT Pub. No.: WO2014/140547
PCT Pub. Date: Sep. 18, 2014

(65) Prior Publication Data
US 2016/0027340 A1 Jan. 28, 2016

Related U.S. Application Data

(60) Provisional application No. 61/775,932, filed on Mar. 11, 2013.

(30) Foreign Application Priority Data

Mar. 11, 2013 (CA) .................................. 2808936

(51) Int. Cl.
*G09B 23/30* (2006.01)
*G09B 23/28* (2006.01)
(Continued)

(52) U.S. Cl.
CPC ............ *G09B 23/286* (2013.01); *A61B 6/583* (2013.01); *G01R 33/58* (2013.01); *G09B 23/303* (2013.01);
(Continued)

(58) Field of Classification Search
CPC .... G09B 23/286; G09B 23/303; A61B 6/583; A61B 6/584; A61B 8/587; A61B 2017/00716; A61B 2017/00725
See application file for complete search history.

(56) References Cited

U.S. PATENT DOCUMENTS 8,188,416 B2 * 5/2012 Borenstein ............. A61B 6/583
250/208.1
8,613,621 B2 * 12/2013 Hendrickson ........ G09B 23/303
434/267
(Continued)

FOREIGN PATENT DOCUMENTS

WO 2014/140547 A1 9/2014

OTHER PUBLICATIONS

Chiribiri et al., "Dynamic simulation of first pass myocardial perfusion MR with a novel perfusion phantom", Journal of Cardiovascular Magnetic Resonance, 2011, vol. 13 (Suppl 1):O43; 2 pgs.
(Continued)

*Primary Examiner* — Justin Olamit

(57) ABSTRACT

The invention relates to a phantom device for reproducing the fluid perfusion in a body, said device comprising a phantom organ that may be introduced into a scanner, said phantom organ comprising a housing in which are defined a plurality of fluid channels, suitably of differing cross-sectional areas; a feed tube arranged to supply liquid to a first end of all of said channels and means for collecting liquid from the other end of the channels. Alternatively or additionally, the device may comprise an element comprising a
(Continued)

phantom heart through which fluid can flow, wherein the phantom heart comprises a first chamber representing a right atrium which is arranged to receive fluid from a fluid supply, a second chamber representing a right ventricle which receives fluid leaving said first chamber, a third chamber representing a left atrium which receives fluid leaving the second chamber and a fourth chamber representing left ventricle which receives fluid leaving the third chamber; and wherein a phantom thoracic system is interposed between the second chamber and the third chamber.

Uses of the device in quality control, validation or calibration of monitoring devices such as magnetic resonance (MR) or computerized tomography (CT) scanners, in teaching or training of machine operatives or for research purposes including for research into scanners, scanning techniques or reagents such as contrast agents used in such processes, form further aspects of the invention.

21 Claims, 10 Drawing Sheets

(51) Int. Cl.
*A61B 6/00* (2006.01)
*G01R 33/58* (2006.01)
*A61B 17/00* (2006.01)
*G01R 33/563* (2006.01)

(52) U.S. Cl.
CPC .............. *A61B 2017/00716* (2013.01); *G01R 33/56366* (2013.01)

(56) References Cited

U.S. PATENT DOCUMENTS

| | | | |
|---|---|---|---|
| 2003/0086535 | A1 | 5/2003 | Teppaz et al. |
| 2008/0108930 | A1* | 5/2008 | Weitzel .............. A61B 5/02152 604/5.04 |
| 2009/0316972 | A1 | 12/2009 | Borenstein et al. |
| 2011/0293074 | A1 | 12/2011 | Coolens et al. |

OTHER PUBLICATIONS

Chiribiri et al., "Perfusion Phantom: An Efficient and Reproducible Method to Simulate Myocardial First-Pass Perfusion Measurements With Cardiovascular Magnetic Resonance", Magnetic Resonance in Medicine, 2012; 10 pgs.

Christian et al., "Estimation of Absolute Myocardial Blood Flow During First-Pass Mr Perfusion Imaging Using a Dual-Bolus Injection Technique: Comparison to Single-Bolus Injection Method", Journal of Magnetic Resonance Imaging, 2008, pp. 1271-1277, vol. 27.

Christian et al., "Absolute Myocardial Perfusion in Canines Measured by Using Dual-Bolus First-Pass MR Imaging", Radiology, 2004, pp. 677-684, vol. 232, No. 3.

Driscoll et al., "Development of a dynamic flow imaging phantom for dynamic contrast-enhanced CT", Medical Physics, 2011, pp. 4866-4880, vol. 38, No. 8.

Ferreira et al., "Measurement of Myocardial Frequency Offsets During First Pass of a Gadolinium-Based Contrast Agent in Perfusion Studies", Magnetic Resonance in Medicine, 2008, pp. 860-870, vol. 60.

Ishida et al., "Absolute Blood Contrast Concentration and Blood Signal Saturation on Myocardial Perfusion MRI: Estimation From CT Data", Journal of Magnetic Resonance Imaging, 2009, pp. 205-210, vol. 29.

Ishida et al., "Development of a universal dual-bolus injection scheme for the quantitative assessment of myocardial perfusion cardiovascular magnetic resonance", Journal of Cardiovascular Magnetic Resonance, 2011, 13 pgs.; vol. 13.

International Search Report and Written Opinion from related International Application No. PCT/GB2014/050705, dated Jul. 15, 2014; 9 pgs.

Jerosch-Herold et al., "Magnetic resonance quantification of the myocardial perfusion reserve with a Fermi function model for constrained deconvolution", Medical Physics, 1998, pp. 73-84, vol. 25, No. 1.

Makowski et al., "First-Pass Contrast-Enhanced Myocardial Perfusion MRI in Mice on a 3-T Clinical MR Scanner", Magnetic Resonance in Medicine, 2010, pp. 1592-1598, vol. 64.

Schuster et al., "An isolated perfused pig heart model for the development, validation and translation of novel cardiovascular magnetic resonance techniques", Journal of Cardiovascular Magnetic Resonance, 2010, 9 pgs., vol. 12.

Wilke et al., "Myocardial Perfusion Reserve: Assessment with Multisection, Quantitative, First-Pass MR Imaging", Cardiac Radiology, 1997, pp. 373-384, vol. 204.

Zierler, "Theoretical Basis of Indicator-Dilution Methods for Measuring Flow and Volume", Circulation Research, 1962, pp. 393-407, vol. 10.

* cited by examiner

PERFUSION PHANTOM DEVICE

FIELD OF THE INVENTION

The present invention relates to a perfusion phantom device that models blood perfusion in organs in the human or animal body for contrast imaging applications. In addition the invention relates to a system which relies on flow modelling in the aorta and 4-chamber heart to generate a physiological dilution curve of the contrast agent during a first pass. Uses of the device in quality control, validation or calibration of monitoring devices such as magnetic resonance (MR) or computerised tomography (CT) scanners, in teaching or training of machine operatives or for research purposes including for research into scanners, scanning techniques or reagents such as contrast agents used in such processes, form further aspects of the invention.

BACKGROUND

Techniques such as magnetic resonance (MR) scanning, computerised tomography (CT) scanning and ultrasound scanning are widely used diagnostic tools for a wide range of medical investigations.

For instance, the potential use of computed tomography (CT) for the assessment of myocardial perfusion has long been recognised. However, only recently has the advent of fast multi-slice CT technology resulted in potential widespread clinical application. The most prevalent method of CT perfusion (CTP) is a single time point comparison of myocardial contrast densities at rest and under pharmacological stress.

Myocardial perfusion is a major determinant of cardiovascular risk and is an essential tool for the guidance of interventional strategies. Magnetic resonance perfusion (MRP) represents a highly accurate clinical perfusion imaging technology, with higher spatial resolution than single photon emission computed tomography (SPECT) and excellent correlation with invasive fractional flow reserve (FFR) data.

First-pass myocardial MR perfusion has become a reliable tool for the diagnosis of myocardial ischemia. Although myocardial perfusion MR images are usually evaluated by visual assessment or by semi-quantitative approaches, quantitative analysis and absolute quantification have also been described and may permit a more accurate assessment of patients with heart disease, particularly those with three-vessel coronary artery disease. Quantitative analysis was initially proposed more than a decade ago and has achieved a recognized role as an investigational tool. However, it has not been adopted into clinical routine thus far. One of the main reasons is the lack of standardization of the analysis methods which is partly due to the lack of a gold standard for validation of the results. Novel techniques are currently developed using combinations of numerical simulations, animal studies and human trials.

Synthetic data simulate the arterial input function (AIF) and myocardial signal intensity (SI) curves at different perfusion rates. Such simulations are intended as benchmarks for deconvolution methods under controlled conditions and known simulated perfusion rates. Though extensively used in the past, these simulations lack standardization and vary from one study to another, hampering comparison of the results between different sites. Furthermore, simulated data do not completely address scanning artefacts (like saturation or susceptibility effects) and ignore spatial relations within the images. Moreover, the level of noise in the data is simulated as well. While simulations allow isolation of the deconvolution problem, they could lead to the development of analysis methods that are not applicable to a real-world scenario. Moreover, no gold standard validation is available and the development of new sequences or novel MR hardware is precluded.

To partially overcome these limitations, vials containing water and Gadolinium in different concentrations have been used to acquire MR perfusion images and calculate signal-to-noise ratio and signal saturation for different spin-lattice relaxation time (T1) values of the samples (Ferreira et al., Magn Reson Med 2008, 60, 860-897; Ishida et al., J Magn. Reson Imaging 2009:29:205-210).

These methods allow the acquisition of real MR data, testing and comparing novel sequences and hardware. However, the SI curves reconstructed from the images result from simulations and quantitative results lack validation against true perfusion measurements. Finally, these static phantoms do not allow the comparison between different schemes of contrast agent injection and do not allow any simulation of the relevant physiological parameters.

Recently, a dynamic flow-imaging phantom has been described to provide reproducibility assessment and validation of dynamic contrast enhanced computed tomography (CT) (Driscoll et al., Med Phys. (2011) 38 (8)). This system, which is potentially MR compatible, mimics realistic time attenuation curves by modulating a contrast injection pump and the ratio between the flow in the main circuit and in a compartment providing a simulation of the tissue response curve. In this study, the CT flow phantom was validated using mathematical models including the control parameters of the system rather than by measuring the flow across the sections of the circuit and the aim was to produce reproducible time attenuation curves for the comparison and assessment of the reproducibility using different CT scanners. The validation of quantitative perfusion measurements was not the main purpose of the CT flow phantom.

A further phantom described in US2009/0316972 uses microengineering to produce a complex model of the microvascular system, useful for the characterisation of perfusion in microvascular networks.

Animal experiments have been used to validate semi-quantitative and true quantitative assessments of myocardial perfusion. These models offer realistic and physiological generation of the signal and allow invasive procedures, such as microspheres injection, for validation of the results. However, the high costs and ethical and logistic considerations limit their applicability.

To overcome these limitations in part, some novel preclinical models have been recently developed. Makowski et al (Magn Reson Med 2010; 64:1592-1598) have described a method of performing first-pass MR perfusion imaging in rodents, using the k-t principal component analysis techniques and a clinical 3T MR scanner. The availability of many transgenic models of cardiovascular disease makes this method particularly useful. However, issues of animal usage remain.

Schuster et al. (J. Cardiovascular Magn Reson 2010; 12; 53) have also described a novel explanted and blood perfused pig heart MR compatible model to develop and validate perfusion acquisitions. This model offers much greater control over physiological parameters and better reproducibility compared with in-vivo preparations although it is less physiological. This isolated pig heart model can be studied in a clinical scanner. In addition, the porcine heart is of comparable dimensions to a human heart. These factors facilitate the development, validation and translation of new perfusion methods. However, operating this experimental model in a clinical scanner is associated with higher costs and requires considerable preparation times, and will therefore probably be restricted to the validation of pre-developed methodology.

Human studies should in theory offer the best setup for the validation of novel MR perfusion methods. Though several studies have been performed comparing the diagnostic accuracy of MR perfusion with coronary angiography and fractional flow reserve (FFR) assessment, the validation of quantitative perfusion assessment can only be performed by comparing these methods in a randomised controlled clinical trial with a measure of outcomes.

There is a need for perfusion phantom hardware capable of simulating the process of first pass perfusion in a highly controllable and reproducible way and thus provide true physical validation of quantitative perfusion methodologies such as MR and CT.

The applicants have devised a device that reproduces physiological features in a simple manner that allows perfusion studies to be carried out in a consistent manner, to allow for modelling by techniques such as MRI and CT.

SUMMARY OF THE INVENTION

According to a first embodiment of the present invention there is provided a phantom device for reproducing fluid flow and perfusion in a body, said device comprising a phantom organ that may be introduced into a scanner, said phantom organ comprising a housing in which are defined a plurality of fluid channels;
a feed tube arranged to supply liquid to a first end of all of said channels; and
means for collecting liquid from the other end of the channels.

By providing a phantom with multiple channels through which liquid flows, blood flow through an organ in the body may be mimicked, thus leading to similar contrast perfusion results. The channels will be sized to suitably replicate the blood flow in the particular organ that is required to be investigated.

In a particular embodiment, at least some of the channels are of a first cross-sectional area and at least some other channels being of a reduced cross-sectional area such that the rate of fluid flow through said other channels is reduced compared to the rate of fluid flow through channels having said first cross-sectional area. In this embodiment, inherently variable flow in one direction is achieved, and so physiological kinetic perfusion compartments similar to those found in the vascular system of a real organ are reproduced. Therefore, imaging studies carried out using this device in conjunction with a contrast reagent will be analogous to those found in an actual organ.

The phantom device must be made of a material that may be introduced into a scanner. Thus, for instance, where the scanner is an MR scanner, the phantom organ may be constructed of a plastics material such a polypropylene, polyvinylchloride, poly(methylmethacrylate), silicone or other materials not showing ferromagnetic properties which might affect MR image quality or MR compatibility. Furthermore, the plastics material must not bind to the contrast agent used in the scanning process since this may get trapped inside. When the scanner is a CT scanner, suitable plastics may include polysulphones as are used in the fibres of dialysis filters, although these may not be used in MR scanning where for instance gadolinium is used as the contrast agent, because of the binding properties as mentioned above.

The channels are suitably impermeable although they may have some degree of permeability. In some embodiments, the material of the channels is rigid to ensure that the position of the channels remains steady during the imaging process. However, it is possible that in other embodiments, they may have a degree of elasticity so as to more accurately reflect physiological differences caused for instance by increases in fluid pressure or movements, for instance caused by breathing, cardiac contraction and posture or postural movements that may occur in a clinical situation.

The channels, which may be of different size and optionally also shape, will suitably be aligned in a parallel relationship within the housing.

Suitably, the channels are arranged to form a three-dimensional structure, and the resulting complex of channels will constitute at least two different 'compartments' with different diameter for the flow to occur, mimicking blood flow in the tissue of a particular organ. Suitable organs will include a myocardium, a liver, a kidney, a skeletal muscle or a brain.

The first cross sectional area will be such as to mimic blood flow in the microcirculation of the tissue. Thus channels may suitably have a cross sectional area of from 0.01 mm to 20 mm$^2$, such as 0.5 to 20 mm$^2$, for example from 6 to 8 mm$^2$ such as around 7-7.5 mm$^2$. The second cross sectional area will be such as to mimic contrast agent diffusion in the particular tissue being replicated by the phantom, for instance by allowing a parallel albeit reduced flow compared with the first cross sectional area. Different arrangements of first and second cross sectional area are possible, in order to modulate the relative speed of flow in each compartment, with the second cross sectional area ranging from 1% to 100% of the size of the first cross sectional area. In a particular embodiment, at least some of the second cross sectional area is reduced, for example in the range of from 1% to 99%, for instance from 1-90%, such as from 1-75%, including from 5-50% of the size of the first cross sectional area. Thus for instance, where the phantom organ represents a phantom brain, all channels within it will be of substantially equal size, because in-vivo there is no extravasation of contrast and therefore no second compartment to mimic. However, for other phantom organs such as a phantom myocardium, a phantom liver, a phantom kidney or a phantom skeletal muscle, at least some channels will be of reduced cross-sectional area to ensure that the second compartment is present to better mimic blood flow. There will suitably be a relatively large number of channels in any individual housing depending upon the size of the housing. Thus for instance, there is suitably at least 5 for example from 5 to 500 channels, for instance from 50-200 channels such as from 100-150 channels having the first cross-sectional area and a similar amount of channels of smaller cross sectional area contained within the housing to provide a suitable flow profile that mimics flow within the tissue of an organ. Such an arrangement may take many forms and may be prepared in various ways, including for instance use of three-dimensional printing techniques to produce a housing including the required number and arrangement of channels or the channels alone for insertion into a suitable housing.

However, in a particular embodiment, the plurality of channels of a first cross-sectional area are provided by a plurality of tubes collected together within a housing so that they are directly in contact with adjacent tubes. In this way, the small and variable spaces between the tubes constitute the channels of reduced cross-sectional area. In this embodiment therefore, the blood flow in the microcirculation of the tissue is represented by the flow inside the parallel channels, whilst contrast agent diffusion in the tissue is mimicked in this particular embodiment by flow through the variable but generally smaller spaces formed between one round channel and its neighbours.

In order to achieve the required flow characteristics necessary in first-pass perfusion methods, liquid should be delivered to the liquid receiving ends of all the channels. Delivery to each of the channels can be arranged to occur substantially simultaneously or it may be applied to different channels at different times, so as to increase flow inhomogeneities. In one embodiment, a liquid receiving chamber is provided at one end of the housing, encasing all the first ends of all the channels. Liquid from the feed tube is supplied into this chamber where it flows into all of the channels. If the ends of the channels are all aligned, liquid will enter each of them at substantially the same time. However, if they are misaligned, flow into each channel will be staggered slightly and so inhomogeneity of the flow may be increased as a result.

In a particular embodiment, the device of the invention comprises more than one, and suitably two phantom organs as described above. In a particular embodiment, the device may comprise three or more phantom organs. In particular, the flow through each organ is independently controllable. The provision of additional phantom organs may be advantageous when the device is used for calibration and quality control purposes as outlined further below, since the signal detectable in each organ provides a distinct datapoint for signal vs perfusion or flow rate, and any divergence from the expected linearity of those points can be identified. Each of the phantom organs is fed by a common liquid supply through separate branches from the feed tube, but the rate of flow through each of said phantom organs is suitably separately controllable for example by providing a filter or diaphragm over the channel outlets to limit the flow in that organ, or by means of a control device, such as a roller pump, arranged downstream of each of said phantom organs.

In this case, the means for collecting liquid from the channels will consist of an independent pipe for each phantom organ. Where the scanner is an MR scanner at least, any control devices such as roller pumps may have to be located outside of the scanner room to avoid interference with a scanning process. However, this can be simply achieved by providing pipes of suitable length. In this way, flow through organs at different flow rates can be accurately and directly compared. Thus for example, the flow rate in one phantom organ can be kept constant and used as a reference standard against which the results obtained in the other phantom organ at variable flow rates may be compared.

In a particular embodiment, the device can model the dilution of contrast agent during the first pass across the vascular structures of the chest, including the heart that occur in vivo in the heart following the injection of contrast media. In order to achieve this, the device comprises a further element that may be introduced into a scanner, said further element comprising a phantom heart into which liquid may be supplied, and which is provided with a tube that carries the liquid out of the heart representing an aorta. Whilst in some embodiments, the tube representing the aorta may be a simple tube, it may, in some instances comprise a realistic model of the vessel, obtained using a technique such as 3D printing. Such tubes may reproduce certain pathological features (i.e. narrowings—stenosis—or dilatation—aneurysms). This is particularly relevant for the teaching phantom and to simulate the hemodynamic consequences of vascular abnormalities of organ tissue perfusion. In such cases, kits may be supplied for use in conjunction with the devices of the invention, the kits comprise a plurality of tubes suitable for use in the device as the simulated aorta, and at least some of these tubes are modified so that the replicate pathological features such as those described above that may be present in an aorta in vivo.

The feed tube for the phantom organ branches off from this 'aorta' tube at a distance therealong that substantially replicates the distance along the aorta at which it joins blood vessels feeding an organ corresponding to the phantom organ. In this way, a bolus of contrast agent injected into the liquid upstream of the phantom heart will be dispersed through the device and in particular through the vascular structures corresponding to the chest and the heart the phantom organ in a manner similar to that which may occur in vivo, before the feeding tube delivers part of the flow to the phantom organ.

The phantom heart suitably comprises a first chamber representing a right atrium which is arranged to receive fluid from a fluid supply, a second chamber representing a right ventricle which receives fluid leaving said first chamber, a third chamber representing a left atrium which receives fluid leaving the second chamber and a fourth chamber representing left ventricle which receives fluid leaving said third chamber before delivering it to the tube representing an aorta. The volumes of the respective chambers are selected to reflect the volumes of the heart of a patient. This may vary depending upon the patient. A reasonable range of volumes for the right ventricle and the left ventricle including all abnormal and normal subjects is 20-300 mL/m$^2$, where m$^2$ relates to the body surface area of the hypothetical patient. Similarly, atrial chambers in a living heart will be in the range of from 20-100 mL/m$^2$. Typically this will equate to a chamber volume in the range of from 10-180 ml, for instance from 100-140 ml. Thus different sized phantom hearts may be used to mimic pediatric hearts or compromised hearts as may be found in patients suffering from heart failure, as compared to a normal heart.

In a particular embodiment, fluid leaving the second chamber flows through an element representing a phantom thoracic or pulmonary system before it enters the third chamber. Such elements may comprise a simple tube or it may comprise a micro- or macro-fluidics structure that mimics the blood flow through the pulmonary system more closely.

The phantom organ may be designed and positioned in the system so as to represent a range of organs including a phantom myocardium, a phantom liver, a phantom kidney, a phantom skeletal muscle or a phantom brain. In order to achieve this, it is preferable to ensure that the ratio between the first cross-sectional area and the reduced cross-sectional area of the channels mimics as accurately as possible the tissue characteristics of the target organ in so far as they relate to contrast agent diffusion. In addition, the branching point of feed tube from the aorta in the phantom device is selected so as to resemble that which occurs in vivo in the anatomy.

The idea of using a phantom heart that is constructed to mimic a physiological heart for the purposes of the perfusion studies is new to the applicant. Thus in a second embodiment the invention provides a phantom device for reproducing the fluid perfusion in a body, said device comprising:

an element that may be introduced into a scanner, said element comprising a phantom heart, through which fluid can flow, wherein the phantom heart comprises a first chamber representing a right atrium which is arranged to receive fluid from a fluid supply, a second chamber representing a right ventricle which receives fluid leaving said first chamber, a third chamber representing a left atrium which receives fluid leaving the second chamber and a fourth chamber representing left ventricle which receives fluid leaving the third chamber;

a phantom thoracic or pulmonary system interposed between the second chamber and the third chamber;

a tube representing an aorta arranged to receive liquid from said fourth chamber:

a phantom organ through which fluid can flow, a feed tube for said phantom organ, which branches off from said aorta tube at a distance therealong that substantially replicates the distance along the aorta at which it joins blood vessels feeding an organ corresponding to the phantom organ; and means for collecting liquid that has flowed through the device.

In such devices, the arrangement of the phantom organ or organs will suitably be as described above in respect of the first embodiment of the invention, but other arrangements are possible. In particular, for CT scanning, a filter as used in dialysis may provide a suitable phantom organ, as the dialysate chambers may be filled with a liquid such as a calcium chloride solution to facilitate a broad-spectrum photon absorption.

In one embodiment, the phantom heart could be produced with a structure and shape which reproduced the anatomy observed in vivo. This would be particularly useful when the device is used for teaching purposes. In this case, the arrangement of the elements of the device, and in particular the first chamber representing a right atrium, the second chamber representing a right ventricle, the third chamber representing a left atrium and a fourth chamber representing a left ventricle may be shaped to resemble those parts of the heart, and assembled together accordingly. Such elements may be produced by various techniques, including for example 3D printing.

Liquid that has flown through the device either through the phantom organ or the tube representing an aorta may be passed through flow meters to check the flow rates and drained to waste either together or in separate streams (open circuit configuration). The number of flow meters will be determined by the measurements required. For example, in order to measure the difference between the cardiac output and absolute flow across the organs, it is appropriate to include individual flow meters to measure the output from each organ as well as the output from the aorta tube. However, if the device is required only to measure total flow across the cardiac chambers (cardiac output), the outputs from all of these can be fed through a single flow meter. In a particular embodiment however, individual flow meters for each organ are provided and the nature of the measurements modified by changing the connections so that, if required, the outputs from each element pass through a single flow unit to provide a direct measurement of the total output. Alternatively, the liquid can be recycled across the system (close circuit configuration), either before or after removal of the contrast agent. In this case, contrast agent may be extracted from the liquid by dialysis methods. Such systems may be particularly useful where the liquid is other than water. Where the contrast agent is not removed, the baseline level of contrast agent in the system will increase and will have to be checked at each pass, in particular by scanning the liquid before injection of more contrast agent.

If required, liquid leaving the phantom organ from the channels of the first cross-sectional area such as the multiple tubes may be collected separately from that which has passed through the smaller channels. This may be achieved for example by addition of a collection chamber through which the tubes pass but which collect liquid from the smaller channels defined by the spaces between the tubes. The collection chamber will be drained separately from the tubes and so the relative flow rates through the different channel types can be checked and also, if required, independently regulated. The ability to independently regulate the flow rates through the different types of channel is a useful facility and allows the device to be designed to more closely characterise different tissue types. For instance, the relative flow rates through the large and small tubes to simulate the heart is different to that in say a brain, and by regulating the flow rates through the tubes and the spaces between the tubes in the device of the invention, the device may be adapted to more accurately reflect this.

For example, normal brain tissue behaves as a single-compartment during first-pass of contrast, as the cerebral microcirculation is not permeable to the contrast agent in physiologic conditions. In this case, the flow-rate across the small tubes can be set to zero, and first-pass signal will be generated exclusively by the large tubes, which represent the vascular compartment. In general, the flow-rate through the small tubes will be kept lower than in the large tubes to simulate diffusion from the vascular compartment (large tubes) to the interstitial and extracellular space (small tubes). However, flow across the small tubes could also be set to the same value or even higher than in the large tubes, to simulate different levels of vascular permeability or even active transport of the contrast agent from the vascular to the interstitial and extracellular pharmacokinetic compartment.

Flow meters and manometers used in the device may be analogue or digital in nature. In the case that these are digital, they may be arranged to send data direct to a digital console and to a computer, which then exerts a feedback control on the device.

The relative placement of the chambers of the phantom heart and the one or more phantom organs is suitably such that a single scanner reading plane will encompass both one or more and suitably all of the heart chambers as well as an appropriate plane within the phantom organ. In this context, an appropriate plane will be one which allows the acquisition of the images at a specific level within the phantom organ which depends upon a titration procedure. In vivo, tissue perfusion rate relates to blood flow on the basis of the mass of the tissue perfused. The titration of the phantom organ allows the identification, by means of special imaging markers, of an imaging plane within the phantom organ that corresponds to a known volume between the point where the input function is measured (i.e. in the aorta) and the imaging plane including the phantom organ. Titration can be performed in a variety of ways that would be apparent to a skilled person. One option is performed by weighing the phantom organ when held in vertical position, and then adding distilled water to the channels up to a predetermined weight, for example 45 g. It is then known that the level reached in the phantom organ equates to a corresponding 'tissue' volume, which in the particular example is 45 ml. The mass of fluid included in this volume constituted the mass that allows calculation of the phantom tissue perfusion rate from the phantom tissue flow rate. Suitable volumes may be anything from 1 ml to 10,000 ml, for example from 1 ml-1,000 ml. In general, the volume is kept as low as possible, as other confounders may arise with higher volumes.

If required, the phantom organ may be shaped to physically resemble the anatomical structure of the target organ. For instance, as described above, an entire heart may be reproduced, with the phantom organ in this case shaped as the myocardium. Within such a model, the channels in particular areas of the phantom myocardium may optionally be closed or blocked to reproduce the appearance of a myocardial ischaemia in the resultant scan. Alternative shaping of the various chambers can be effected so that they reflect the actual anatomical structure of other organs as required. Again, techniques such as 3D printing can be used in the production of these organs. This embodiment may be particularly useful with the device is used for training purposes or in the development of post-processing software.

In a particular embodiment, features of the device, in particular the phantom organs and/or the phantom heart are enclosed in a transparent container. This will prevent leaks of water and assist in the preparation of the experiment by providing a support for tubing and coils etc.

In use, the device is positioned with a scanner such as an MR or CT scanner so that the imaging plane passes through at least the phantom organ or organs and if desired, also through one or more chambers representing the chambers of the heart. Liquid, which may be water, blood or a blood substitute or mimic is pumped into the device from an external pump. In the case of MR scanners, the pump would be required to be located outside the scanner room to avoid interference with the device. Whilst blood or blood substitutes may be used to better reproduce the effects seen in vivo, including the impact these will have on contrast agents, the use of such a liquid would be expensive and may not be justifiable in all circumstances. In this case, water may be liquid used and it is possible to use a reservoir/header tank or mains pressure as the pump to force the water through the device and the phantom organ.

Perfusion rates to replicate physiological conditions will generally be in the range of from 0.1 to 10 mL/min/g of 'tissue'. While the liquid may be supplied at relatively high pressure and the perfusion rate through the individual phantom organs passively controlled by pressure differences within the compartments of the device, in a particular embodiment a downstream control by means of roller pumps (one for each phantom organ) is provided. Optionally also, downstream control means may be used to independently control the flow rates through the channels of first and second cross-sectional area as described above.

The provision of the pumps downstream of the phantom organs means that the volume of the system can be kept low as the amount of 'dead space' within the phantom itself is kept to a minimum. This is advantageous in terms of accuracy of the results and also, ensures that the device more closely resembles a physiological system. In addition, the pumps may be easily located outside of the scanner room, which in some instances, such as where the scanner is an MR scanner, will be essential.

A bolus of contrast material or tracer is added to the liquid at a predetermined point upstream of the phantom organ and the phantom heart when present. Suitable contrast agents or tracers will depend upon the particular scanning technique but include those known in the art which are or which may become commercially available, including agents comprising gadolinium, iron oxides, manganese or iodine based compounds. These are administered at a dosage that depends upon a variety of factors including the nature of the particular contrast agent or tracer used, the formulation of the bolus, as well as the body weight of the patient whose treatment is being replicated. The selection of suitable dosages would be within the understanding of the skilled person.

In a particular embodiment, a means for removing gas bubbles from the liquid fed into the device is also provided, preferably upstream of the point at which contrast agent is added. Such means may comprise for example a bubble trap, which comprises a chamber containing an air space above it, through which the liquid is caused to flow sufficiently slowly to allow any gas bubbles present to rise through the liquid and be captured within the air space. Baffles may be provided to control liquid flow. Various bubble traps are known in the art. The provision of such as trap may improve the reliability of the device.

At one or specified time points thereafter, representative of a first pass of blood through the circulatory system, one scanner image or a series of images are obtained. The time that will be required will vary depending upon the nature of the organ that is being simulated and hence its distance from the site of introduction of the bolus of contrast agent and the heart and other physiological factors such as cardiac output and perfusion rate of the organ. Generally however, scans will be taken no later than 2 minutes from the time of introduction of the contrast agent, and generally at one or more times within the first 60 seconds. Since the liquid flow rates and the distribution volume are known (see titration procedure described above), the perfusion rates can be calculated. The resultant images can therefore be used to calibrate the scanner or validate the existing scanner readings.

The device reproduces results reliably allowing the user to have confidence around the output generated. It may therefore be used for the testing of novel experimental parameters or products such as algorithms and analysis software, as well as in research, development and evaluation of novel contrast agents. For example, the device may be run using a novel contrast agent and the results obtained used to see how the contrast agent behaves in the scanner environment. Similarly, where new algorithms or analysis software are used in relation to the scanner, these may be tested using the phantom device of the invention and the impact on the results obtained determined.

If required, means for moving the device may be provided to simulate the effects of the natural movement of patients, for example, by breathing during an investigation. The device may be used to develop means of dealing with any resultant image distortion that occurs.

Thus a third aspect of the invention provides a method for calibrating or validating a parameter of a scanner, said method comprising placing a device as described above in a scanner so that at least an element of the device is within the imaging plane of the scanner, causing a liquid to flow through the device at a known control rate, carrying out scanning operations using the scanner and relating the results obtained to the parameter of the scanner. Suitably a contrast agent is introduced into the liquid flowing through the device at a point upstream of a phantom organ or phantom heart where present, and scans obtained at predetermined time points thereafter. A baseline scan may be taken before the introduction of the contrast agent if required.

Scanning can be effected using any of the available technologies such as MR, CT, SPECT or Ultrasound, as well as a positron emission tomography (PET) scanner. The scanning operation may also be carried out using X rays.

Research aspects in particular into the use of contrast agents or tracers, for example investigations into dosage regimes or into various bolus formulations, or in the development of novel contrast agents themselves form a fourth aspect of the invention. Such methods involve comprises carrying out the method as described above using the novel or modified contrast agent or tracer and determining how such agents function in the scanning investigation.

The device may also be used as a teaching aid to allow students to become familiar with operation of the scanners and the interpretation of results. Thus, a fifth aspect of the invention provides for the use of the device described above as a teaching aid. The methodology in this case will be similar to that described above in relation to the calibration or validation method, but the parameters may be varied to provide students with a broad insight into the sort of results they may expect to see from a scanning investigation. Experience of using the scanner in a variety of ways can be gained before carrying out any investigations directly on patients.

As illustrated in the examples hereinafter, a perfusion phantom embodying the invention allows reproducible and realistic simulation of first pass perfusion, and to offer true validation of the results of quantitative analysis without the need for lengthy and expensive laboratory analyses. The phantom is cheaper than the competing solutions, all of the equipment can be reused, and the acquisition process is very efficient, as washout of the contrast agent in the open circuit model only requires 60-180 seconds (depending on the set perfusion rate) before a new perfusion experiment can be performed. Efficiency may be increased still further by provision of a separate perfusion or washing channel that can be activated between imaging experiments. This channel is arranged to feed clean water into the phantom to wash away any residual contrast agent to allow a shortened delay of time between acquisitions, resulting in a more efficient scanning procedure. The washing channel is suitably arranged to provide wash liquid such as water directly to the phantom organ such that it is fed directly through all the channels within the phantom organ. It is suitably provided with appropriate control valves so that wash liquid can be applied only when required.

Our data demonstrate that the perfusion phantom provides data suitable for quantification by means of signal de-convolution. Whilst the use of the phantom of the invention may not completely replace the need for animal experiments or human studies, it will allow a reduction of the number of animal studies required to develop and validate novel scanning techniques.

Furthermore, the capability of the perfusion phantom to offer a controlled and highly reproducible simulation of first-pass perfusion, with selective alterations of myocardial blood flow in one or both myocardial compartments, is likely to expedite the development and comparison of different acquisition sequences or hardware or direct comparison of different quantification techniques, which is very difficult to achieve in vivo.

A possible confounding effect in first-pass perfusion quantification is due to bolus dispersion that occurs during the transit through the epicardial vessels to the myocardium. Even though dispersion effects cannot be completely excluded, these can be relegated to a minor role in the setup of the phantom of the invention due to: 1) the physiological design and size of the coronaries and myocardial compartments of the phantom, resulting in physiological flow and perfusion rates; 2) the fixed geometry of the coronaries (alterations of the perfusion rate are generated by changing the speed of the roller pumps downstream the imaging plane and not by alterations of the vascular geometry (stenosis); 3) the use of a continuous perfusion flow, eliminating the risk for temporal variations of dispersion due to the reflection of pressure waves. Moreover, in a particular embodiment pulsatile flow can be achieved by using a different type of pump.

The perfusion phantom of the invention allows reliable, reproducible and efficient simulation of myocardial perfusion. The availability of a direct comparison between the image data and reference values of flow and perfusion will allow rapid development, validation and calibration of accurate quantification methods.

In a particularly preferred embodiment, and in particular where the scanner is an MR or CT scanner or a PET or SPECT scanner, the method of the invention is used to calibrate the scanner. Instrument calibration procedures are distinct from instrument validation procedures, for which phantom devices are typically used in the literature. Validation procedures assume that the instrument (either the imaging scanner or the software used for quantitative post-processing of the data) is intrinsically capable of providing quantitative measurements of perfusion based on an intrinsic property (such as a specific deconvolution algorithm or pharmacokinetic models of contrast agent dynamics during first pass). Validation procedures may for example check the results of software versus a truth measurement—also known as accuracy of the measurement, but will take for granted the existence of a calibration somewhere else in the process. While accuracy control is part of a calibration procedure, they are not the same. The applicants have developed a new and particularly useful calibration procedure, as illustrated in example 7 hereinafter, which uses the phantom device described herein to build a calibration curve, which relates the numerical results of a mathematical operation (deconvolution of signals in the examples) to a physical measurement and allows physical measurements using the instrument.

In this case, it is preferable that at least three phantom organs as described are provided and the flow rates through each is independently controllable, for example using downstream roller pumps as described above. By providing three organs in this way, the calibration of the device can be more accurately checked in a single perfusion pass. In particular, it is to be expected that a linear relationship will occur between flow rates applied and the signal obtained. By providing at least one additional organ, the linearity of the results, and in particular, the linearity of the perfusion measurements with regard to the absolute true perfusion rate, can be confirmed. This linearity is an important parameter and has been described as the most relevant advantage of quantitative methods of upslope or semi-quantitative methods. Any deviation from this will be clear from the provision of at least one additional datapoint in a graph, and thus this will indicate that adjustment of the scanner is required. Thus the method includes an in-built 'quality control' system.

In some embodiments, the device of the invention can be equipped with an ECG simulator. This is a device capable of generating an electric signal similar to that registered as surface ECG from patient. The ECG signal can be used to trigger the acquisition of the images.

In yet further embodiments, the device can be arranged so that it simulates scanning artefacts that may occur. Thus for instance, the device can be modified to reproduce common artefacts which might affect the image quality obtained in vivo. For example, device can be equipped with apparatus to simulate respiratory movements, in one or more directions. This can be achieved in numerous ways, for example by mechanical or pneumatic or hydraulic means. By operating the apparatus during the scanning procedure, the ability of the scanner to deal with the artefacts can be assessed.

Alternatively, the device may be equipped with additional parts to simulate other common types of imaging artefacts, including beam-hardening artefacts in CT as well as attenuation artefacts in PET and SPECT.

DETAILED DESCRIPTION OF THE INVENTION

The invention will now be particularly described by way of example with reference to the accompanying diagrams which are summarised as follows. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

DESCRIPTION OF THE DRAWINGS

FIG. 1A illustrates a device arranged to measure the difference between cardiac output and the absolute flow, and FIG. 1B illustrates an alternative arrangement to measure total flow across the cardiac chambers. Three main units constitute the perfusion phantom: the main pump and the control unit—located outside the MR room—and the MR compatible unit (the phantom) in the bore of the scanner. The main pump generates the water flow across the phantom. Just before the tube representing the vena cava (VC), a three-way tap allows the injection of the contrast agent into the circuit using a clinical power injector. The flow travels across the chambers representing cardiac chambers and the thoracic vessels to reach the tube representing the aorta, where a portion of the flow is directed toward the right and left myocardial compartments. The water flow from the aorta after the take-off of the coronary circulation is then directed back outside the scanner room to the control unit where it is continuously measured by means of a vertical flow meter. The flow from the right and left myocardial compartments is returned in two separate pipes to roller pumps—part of the control unit—that allow fine regulation of the flow across each compartment. At the outlet of each roller pump, a vertical flow meter continuously measures the flow across each myocardium. LA: left atrium; LV: left ventricle; PA: pulmonary artery; PV: pulmonary vein; RA: right atrium; RV: right ventricle. FIG. 1C illustrates an alternative embodiment which includes a third phantom organ, to optimise the calibration potential of the device.

(A) Arterial input function peak signal intensity for different dosages of contrast agent. Dosages representing 0.0005, 0.001, 0.01 and 0.1 mmol/kg of body weight injected in the system under constant experimental conditions (see text for details), producing an increasing amplitude of the arterial input function measured in the aorta.

(B) Myocardial peak signal intensity for different dosages of contrast agent. Dosages representing 0.001, 0.0025, 0.005 and 0.01 mmol/kg of body weight injected in the system with constant myocardial perfusion rate (10 ml/g/min). No saturation effects were observed in the range of concentrations tested.

(C) Dosages representing 0.0005, 0.001, 0.01 and 0.1 mmol/kg of body weight were injected in the system under constant experimental conditions (see text for details), producing an increasing amplitude of the arterial input function measured in the aorta. Saturation effects with clipping of the signal intensity curve are visually observed at 0.1 mmol/kg of body weight. Myocardial signal intensity (SI) curves are represented for the 0.01 mmol/kg of body weight injection. Right myocardium: 2.5 mL/g/min; left myocardium 10 mL/g/min.

Figure 6:
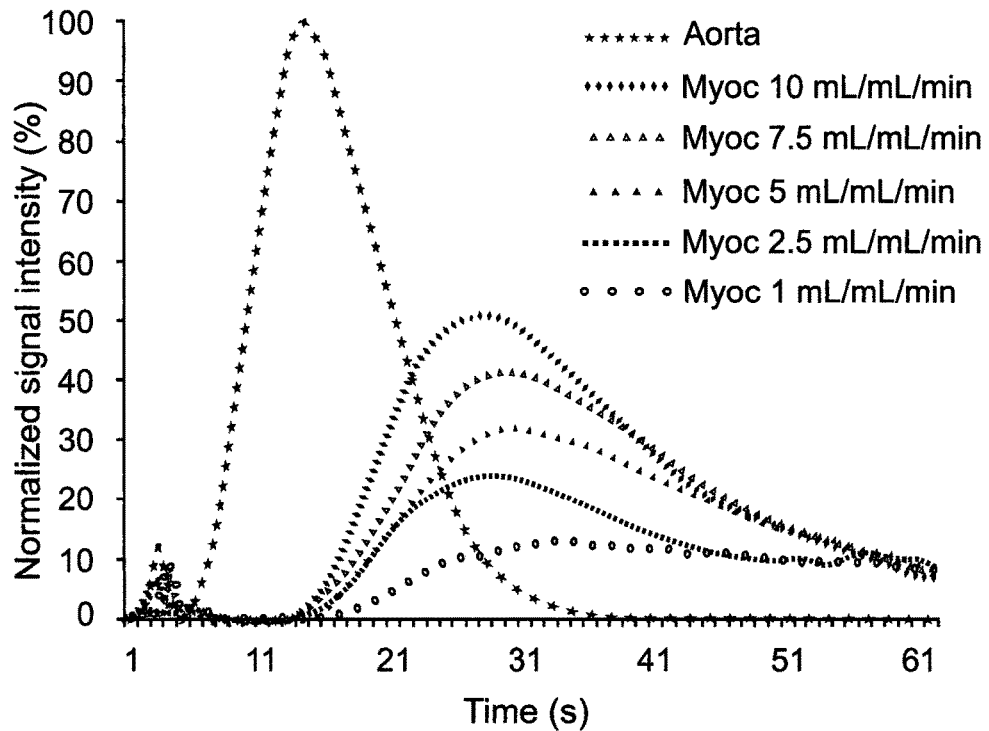

FIG. 6—Response of the system to isolated changes of the myocardial perfusion rate. The graph represents the myocardial signal intensity curves at different perfusion rates (1, 2.5, 5, 7.5, 10 mL/g/min) normalized on the aortic arterial input function.

Figure 7:
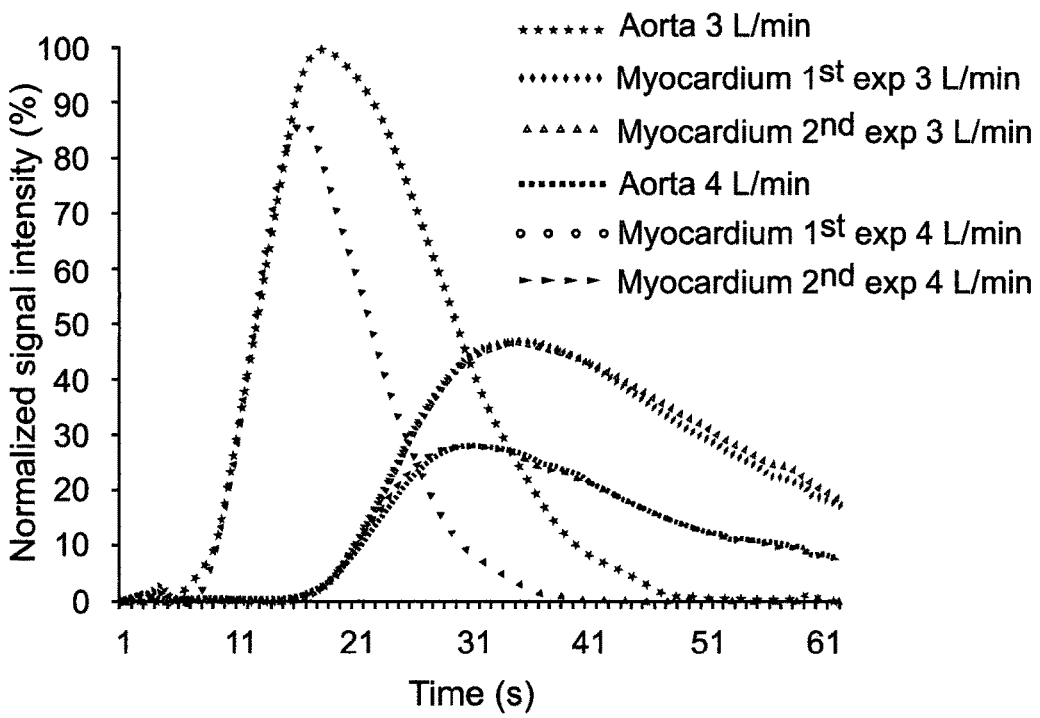

FIG. 7—Response of the system to isolated changes of the cardiac output and reproducibility of the measurements. Each experiment was performed twice with cardiac output at 3 and 4 L/min and demonstrates the effects of different dilution rates on the peak signal intensity and speed of wash-out of the arterial input function (Aorta) an in the myocardial compartment. The experiments were repeated by different operators and on different days, showing a very good reproducibility of the measurements.

Figure 8A:
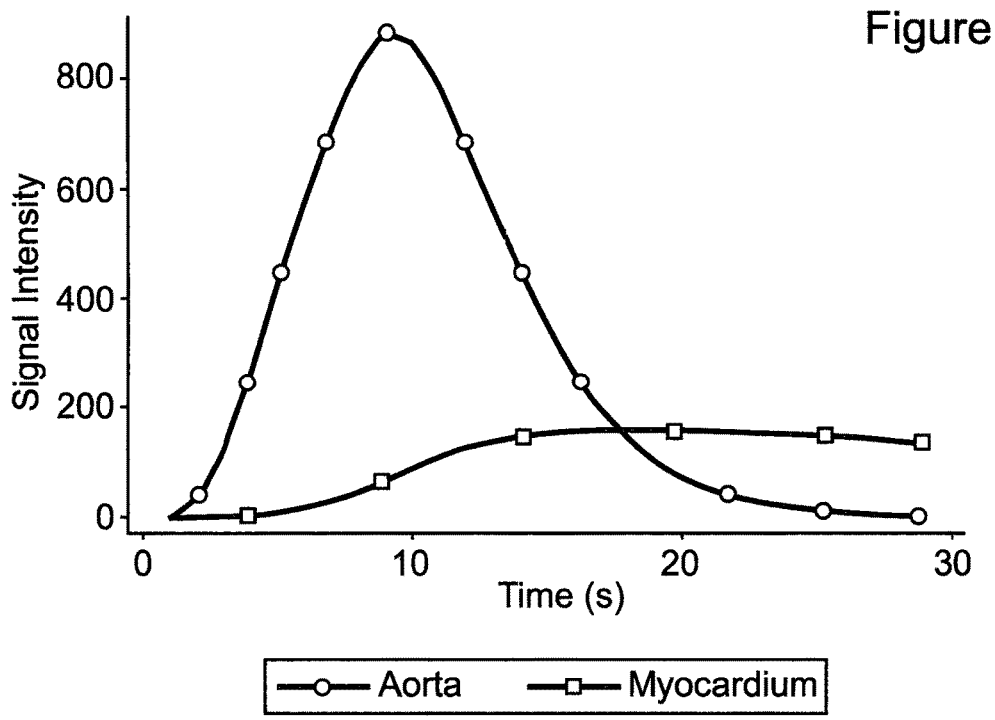
Figure 8B:
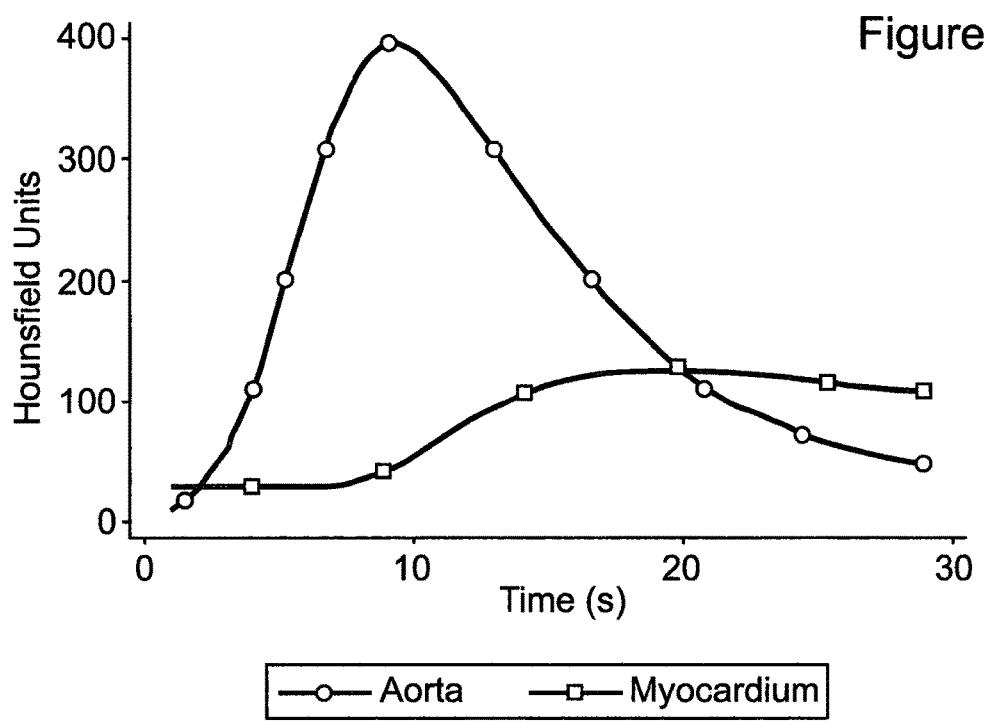

FIGS. 8A and 8B—Results of experiments using the system of the invention—FIG. 8A illustrates MRI phantom perfusion signal intensity and FIG. 8B shows CT Myocardial perfusion phantom attenuation.

Figure 9:
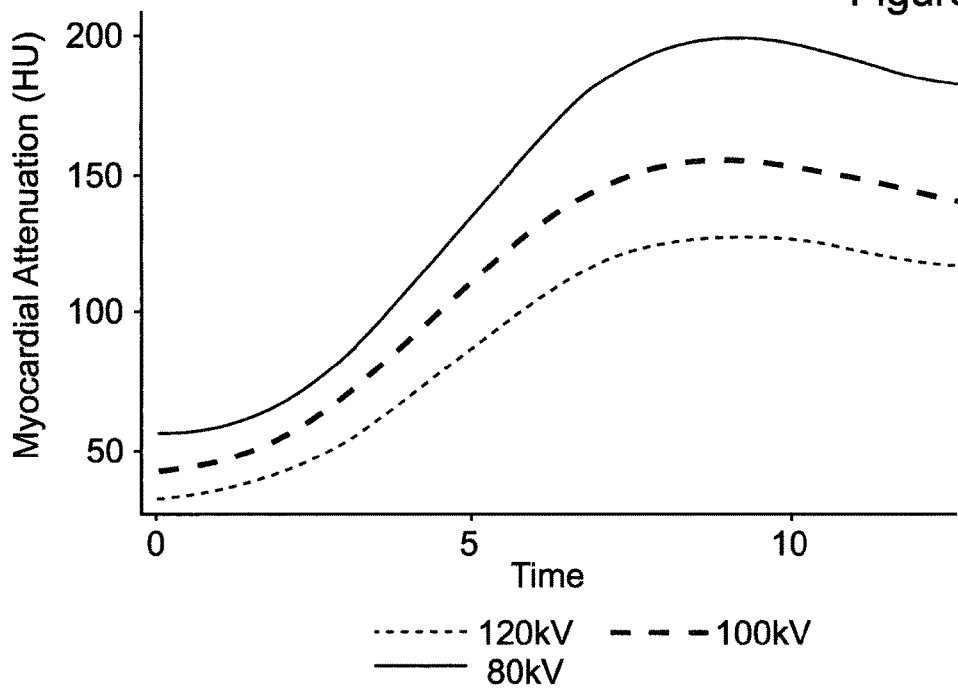

FIG. 9—Results of experiments using the system of the invention—CT myocardial perfusion imaging at various photon energy levels.

Figure 10:
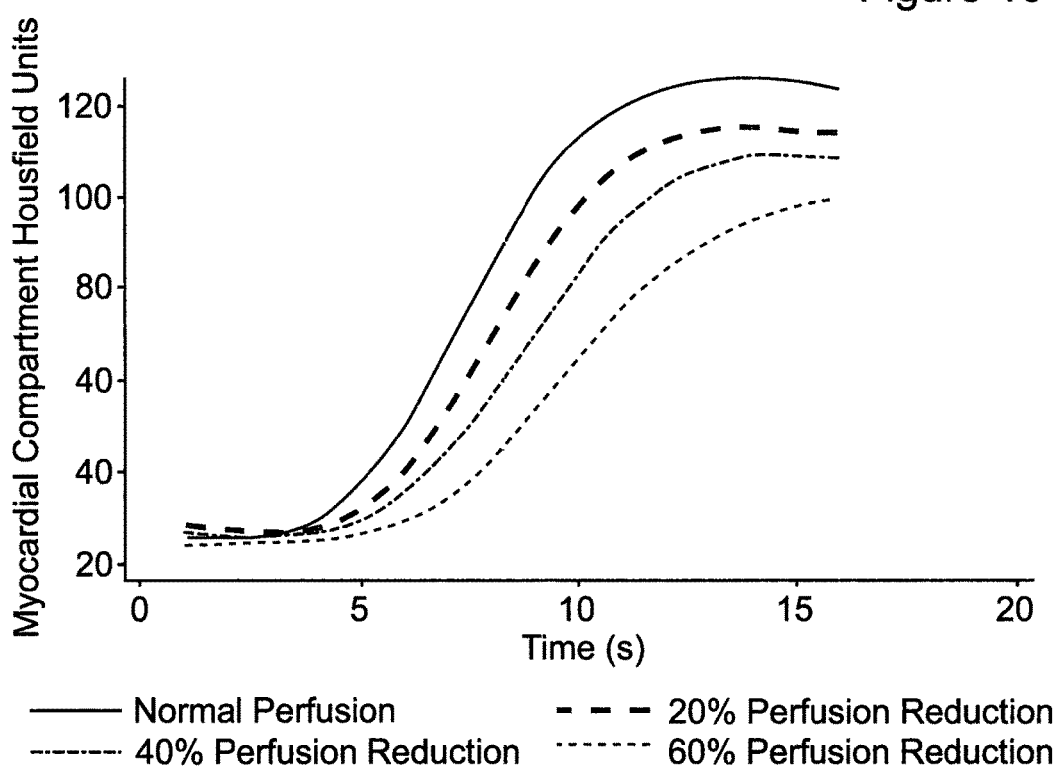

FIG. 10—Results of experiments using the system of the invention—CT myocardial perfusion imaging with simulated perfusion deficits.

Figure 11:
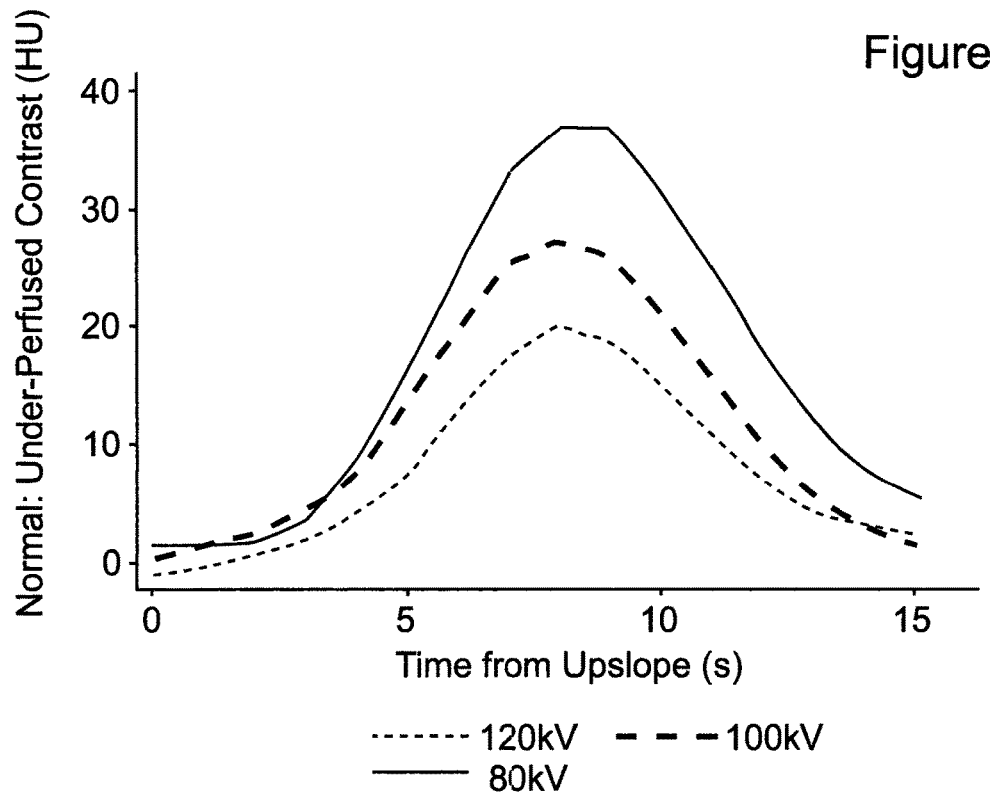
Figure 12:
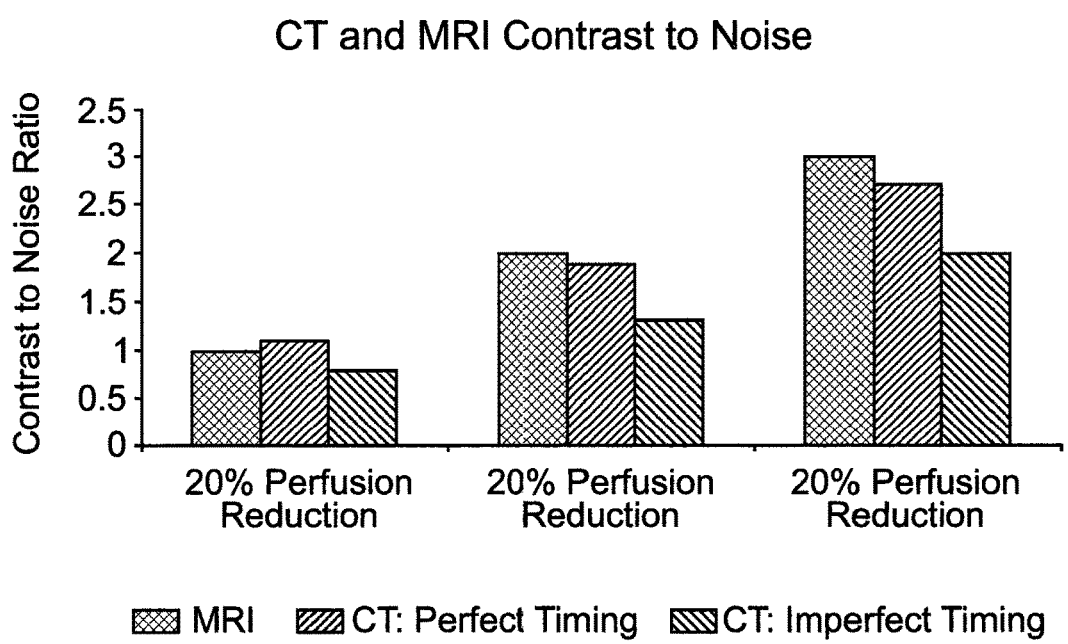

FIG. 11—Results obtained using the system of the invention—CT myocardial perfusion image contrast between normal and 20% perfusion reduction compartments at varied x-ray photon energy FIG. 12—Results obtained using the system of the invention—Image contrast for a perfusion deficit of 20% for MRP and CTP. CTP contrast both with perfect image acquisition timing and an error of 2 heart beats are displayed.

In the following examples, image and statistical analyses were carried out as follows:

Image Analysis

Data were analysed using ViewForum v6.3.1.2 (Philips, Best, Netherlands) modified with software made in-house which allows efficient segmentation of the images and export of the SI curves for analysis. Data were analysed by a researcher who was unaware of the protocol and perfusion rate used in each experiment. Quantification of myocardial perfusion was performed using a Fermi deconvolution method (Jerosh-Herold et al., Med Phys 1998:25:73-84).

Both the extracted AIF $c_{in}(t)$ and myocardial compartment SI curve q(t) values were entered into the deconvolution model that is based on the central volume principle (Wilke et al. Radiology 1997:204:373-384, Zierler Circ Res 1962: 10:393-407):

$$q(t) = \int_0^t c_{in}(t-\tau) \cdot h(t)d\tau = F \int_0^t [c_{in}(\tau) - c_{out}(\tau)]d\tau,$$

in which F denotes perfusion flow and $c_{out}(t)$ the contrast concentrations in the venous outflow. The tissue impulse response h(t) is estimated by using a Marquardt-Levenberg nonlinear least square optimization method to fit a Fermi function with the following analytical expression:

$$h(\tau) = F \cdot \left[\frac{1}{e^{(\tau-\tau_0-\tau_d)k}+1}\right]\theta(\tau_d).$$

In the above equation, F and κ represent indices of the contrast agent influx and efflux parameters, $\theta(\tau_d)$ is the unit step function, $\tau_d$ accounts for the delay time between the appearance of signal in LV blood pool $c_{in}(t)$ and myocardial region of interest q(t) and finally $\tau_0$ characterizes the width of the shoulder of the Fermi function during which little or no contrast agent has left region of interest. This fitting procedure yielded the time curves for tissue impulse response function, h(t), from which perfusion values were calculated as (h(t=0)).

Statistical Analysis

SI curves were compared to assess reproducibility by means of a linear regression analysis using the Pearsons' correlation coefficient. Multiple measurements were compared using the ANOVA test. All data analysis was performed with PASW statistics for Mac 18.0.0 (SPSS, Chicago, Ill., USA).

EXAMPLE 1

Design of the Device

The phantom was designed to simulate dynamic of first-pass myocardial MR perfusion after the injection of a bolus of a Gadolinium-based contrast agent. The system is made up of three main parts: the main pump generating water flow in the circuits located outside the MR room, the MR-compatible unit (the phantom) located in the scanner and the control unit located outside the MR scanner room (FIGS. 1A-C and 2).

The Main Pump

The main pump (1) maintains the water flow across the phantom and was located outside the MR room indicated by the region below the dotted line in FIGS. 1A-C. Various pumps producing continuous or pulsatile flow can be fitted to the system. Alternatively, it can be driven by water pressure from a water tap, as performed in our laboratory in some preliminary experiments (data not shown). Furthermore, the system can be configured as an open or a closed circuit. In the open circuit configuration (FIGS. 1A-C), the system is continuously supplied with clean water from the water mains and the volume of water and Gadolinium flowing back from the phantom is discarded. In this setup, the background signal intensity (SI) values return to baseline in 60-180 s (depending on the myocardial perfusion rate) in preparation for subsequent Gadolinium injections. In the closed circuit configuration, the reflowing water is recycled back through the system, with the effect of increasing background signal as the concentration of contrast agent increases in the circuit. The closed circuit configuration also allows modification of the recirculating perfusate. In this example, data was obtained with the open circuit setup, driven by a constant flow pump (model ISM 405A, Ismatec, Glattbrugg, Switzerland—pump-head model 201-000, Micropump, Vancouver, Wash., USA). By adjusting the speed of the main pump (1), the cardiac output of the phantom can be varied between 2 L/min and 11 L/min. At a simulated heart rate of 60 beats per minute, a cardiac output of 4 L/min corresponds to a stroke volume of 67 mL. As a reference, the same cardiac output in a 60 kg/170 cm patient (body surface area of 1.68 $m^2$) would be equivalent to a cardiac index ranging from 1.2 to 6.6 L/min/$m^2$.

The Phantom

In order to reproduce the dilution of the contrast bolus and its mixing with blood that occurs in the large thoracic vessels and in the heart, the phantom was designed to resemble the anatomy of the thoracic circulation and of the heart of, in this example, a 60 kg human subject (FIGS. 1A-C and FIG. 2, panel A). The inner blood volume of each section was sized to resemble physiological size as closely as possible (Table 1). Moreover, the body-weight adjusted volume of contrast agent administered in each experiment was calculated for this 60 kg value.

For the sake of simplicity, in this example we will refer to each segment of the phantom by the name of the anatomical structure it represents (their technical specifications are listed in Table 1 hereinafter). The core of the system is a four-chamber heart (2) and two cylinders (3,4) representing the myocardial compartments (FIGS. 1A-C and FIG. 2, panel A). The heart comprises a chamber (5) representing a left ventricle (LV) and a chamber (6) representing a right ventricle (RV), each having a volume of 120 mL each. A chamber (7) representing a right atrium (RA) and a chamber (8) representing the left atrium (LA) have a volume of 105 mL each.

The heart (2) receives a positive pressure water flow from a pipe (9) connecting a tube (10) representing the vena cava (VC) to the main pump (1) by way of a manometer (11) acting as the control unit. Just before the tube (10) of the VC (15 cm before the chamber (7)(RA)) a 3-way stopcock (12) allows direct injection of contrast agent which in this case was gadolinium into the water flowing in the circuit. This operation was performed by a clinical power injector (Spectris Solaris, Medrad, Germany), which allows contrast to be administered in the same way as it is for usual clinical protocols.

After the injection, the bolus of contrast agent travels in the water through the chambers and vessels and it is progressively mixed and diluted in water. Similarly to the fragmentation of the bolus of Gadolinium observed in vivo, the system generates the arterial input function (AIF) measured in a tube (13) representing the proximal aorta that can be used for quantification of myocardial perfusion by means of signal deconvolution techniques.

The bolus flows through the chambers (RA and the RV, which is connected to the chamber (8) representing the LA by a silicone tube (14) (FIG. 2, panel A) representing the pulmonary artery and pulmonary vein. After the chamber (6) representing the LV, the flow enters the aortic vessel, where a small polyvinyl-chloride (PVC) pipe (15) gives origin to the coronary circulation that connects to the right and the left myocardial compartments (3,4). A defined volume of the flow (precisely regulated and measured by the control unit) enters both the right and the left myocardial compartments (3, 4) after the bifurcation of the PVC pipe (15) (see below for details about flow/perfusion gold standard measurements).

Both myocardial compartments comprise plastic cylinders (16) (FIG. 3) of 4 cm diameter each containing 124 pipes (17) (not all shown) with a thin (0.1 mm) polypropylene wall and with a diameter of 3 mm. The packing of the pipes (17) within the cylinder (16) means that spaces between the tube form parallel channels (18) but of reduced cross-sectional area. Simulated coronary blood flow enters the myocardial compartments (3, 4) in the direction of the arrows through a lateral inlet chamber (19) at the end of the cylinder (16), ensuring an even distribution of the perfusion flow during first-pass across the entire cross-section of the cylinder (16). Myocardial SI curves are generated in the imaging plane during first-pass of the bolus of contrast agent, which follows two different pathways: inside the pipes (17) (solid black arrow) and with slower speed in the space (18) between one pipe and the others (dotted arrow). Both components generate the dynamic first-pass signal intensity upslope. An imaging plane (20) is located at the level of a marker (21) that identifies a myocardial distribution volume of 45 ml. This value allows the calculation of the gold-standard perfusion rate from perfusion flow measurements.

Figure 3:
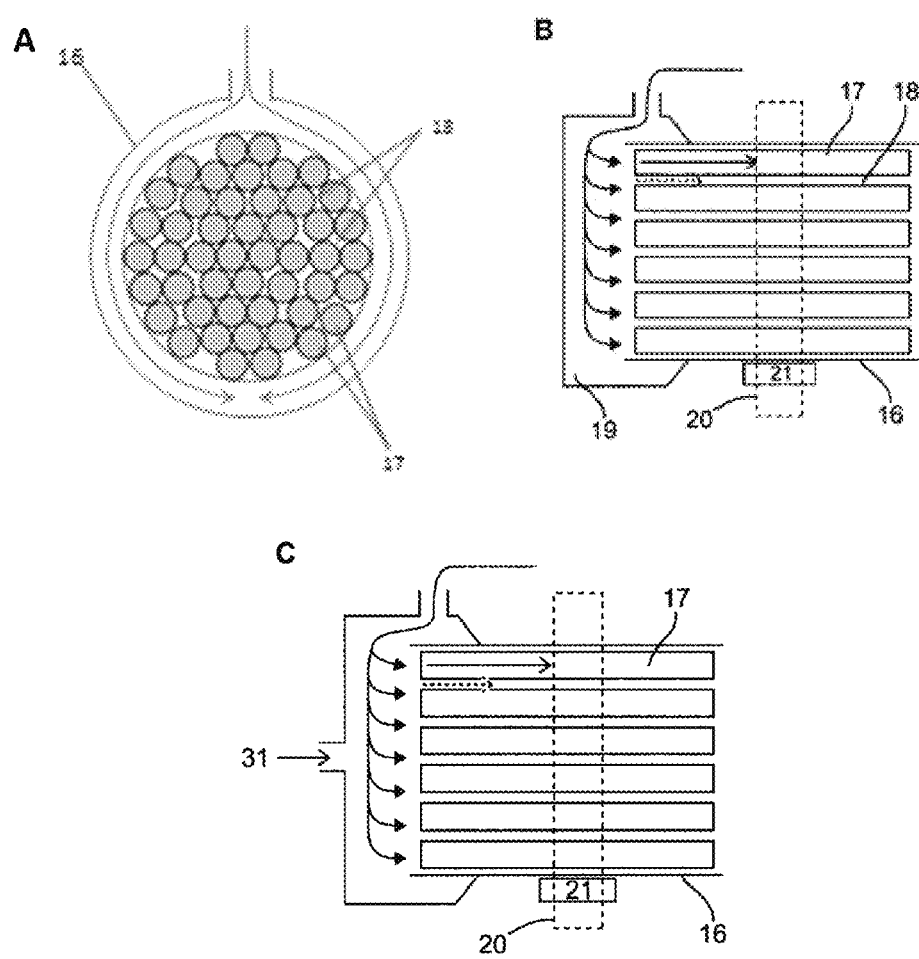
FIG. 3—Schematic representation of the myocardial compartments. A. Short-axis view at the level of the myocardial flow inlet, represented by a lateral opening in the compartment. The simulated myocardial blood flow distributes to a circular space surrounding the inlet of the pipes first and then (B) enters the pipes. These are 124 parallel polypropylene pipes (48 shown in this scheme). (C) Shows a modified form which includes a channel for washing out the contrast agent. Representation not to scale.

In a modified form of the organ shown in FIG. 3, panel C, a channel (31) is provided in an end wall of the phantom organ representing the myocardial compartment and is arranged to supply wash liquid such as water directly through the pipes (17) and the spaces (18) to allow for rapid wash-out of contrast agent between runs.

Two independent pipes collect the water flow from the myocardial compartments (3,4) and return it independently to the control unit (FIGS. 1A-C and FIG. 2, panel B), where flow rates can be accurately measured and controlled in the range of 0.035 to 0.45 L/min.

In order to relate the gold-standard flow rate across the myocardial compartments (3,4) with the measured perfusion rate, the myocardial compartments (3,4) were titrated to define the distribution volume of the contrast agent during first-pass. The distribution volume is the water effectively modifying the distribution of the contrast agent and the characteristics of the SI curves during first-pass and was defined as the volume of water comprised between the point where the aortic AIF is sampled (just before pipe (15), the take off of the coronary circulation) and the myocardial volume preceding and including the imaging plane. Due to the complex geometry of this section, the position of the imaging plane was defined by weighing each myocardial compartment (3,4) (kept in vertical position) and its coronary vessel on a precision scale and adding 45 g of distilled water, corresponding to 45 ml of volume. To facilitate the identification of the correct geometry during scanning, the level corresponding to the imaging plane (20) was marked on the outer surface by a multimodality marker (Multi Modality Marker 3003, IZI Medical Products, Maryland, USA; FIG. 3). The plastic pipes do not have any filtration function and do not constitute a separate compartment for the diffusion of the contrast agent within the myocardial space. Therefore, the myocardial space acts as a single compartment for the distribution of Gadolinium.

Referred to the distribution volume of 45 mL, flow rates ranging from 0.035 to 0.45 L/min correspond to perfusion rates ranging from 0.8 to 10 mL of perfusate/mL of distribution volume/min [mL/mL/min].

Figure 4:
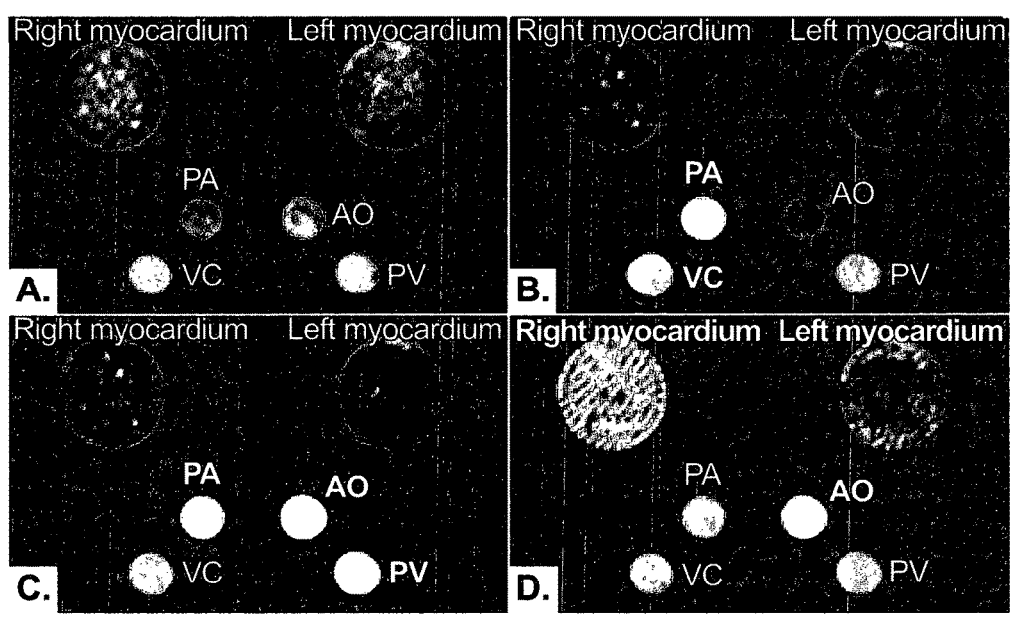
FIG. 4—Example of consecutive dynamics obtained from the perfusion phantom. A. Baseline image, before contrast injection. B. Early image, with signal intensity (SI) increase in the vena cava (VC) and pulmonary artery (PA). C. SI increase in the PA, pulmonary vein (PV) and aorta (AO). C. SI increase in the AO, right myocardial compartment (perfusion rate 10 mL/g/min) and initial signal increase in the left myocardial compartment (5 mL/g/min).

The phantom itself is contained in a plastic box and can be used with any surface array coil used for parallel cardiac imaging. The design of the phantom allows the acquisition of the MR images of the aorta and the myocardial compartments in the same imaging plane (FIG. 4).

The Control Unit

The control unit (FIGS. 1A-C and FIG. 2, panel B) is located outside the MR room and is designed to allow precise measurements of flow in each compartment of the phantom (gold standard reference for perfusion and cardiac output) and fine control of the functional parameters of the system. The control unit receives the forward flow from the main pump (1) and measures the maximum pressure in the water circuit by means of an aneroid manometer (11) (Model EN837, Nuova FIMA, Novara, Italy; FIGS. 1A-C and FIG. 2, panel B). This permits prompt identification of any leakages (pressure drops to zero) or obstructions (pressure rises above 50 kPa). During normal operation, the maximum pressure in the circuit reaches approximately 25 kPa for a forward flow of 3 L/min, and 40 kPa for 4 L/min. After passing the manometer, the forward flow continues towards the VC (10) of the phantom.

The control unit receives the return flow from the phantom via 3 independent pipes representing the distal aortic flow (22); as well as pipes from the right and left myocardial compartments (23, 24).

The distal aortic flow (22) is measured by a vertical flow meter (25) (model 5.800002, Parker, RS Components, United Kingdom) before being discarded or re-circulated through the system in the direction of arrow 26, depending on whether the water circuit is in an open or closed configuration.

The return flow from each myocardial compartment is brought back independently to the control unit where two roller pumps (27, 28) (Model U505, Watson Marlow, Falmonth, United Kingdom) regulate precisely and independently the perfusion rate in each myocardial compartment (3, 4). The roller pumps (27, 28) were positioned distal to the myocardial compartments (3, 4) in order to minimize the dead space between the ascending aorta and the myocardial compartments. Positioning the pumps between the ascending aorta and the myocardium might interfere with the dilution of the contrast agent and therefore affect quantitative perfusion measurements.

At the exit of the roller pumps (27,28), the flow rate in the right and left myocardial compartment lines is measured by 2 vertical flow meters (29, 30) (model S.800003, Parker, RS Components, United Kingdom).

Figure 1A:
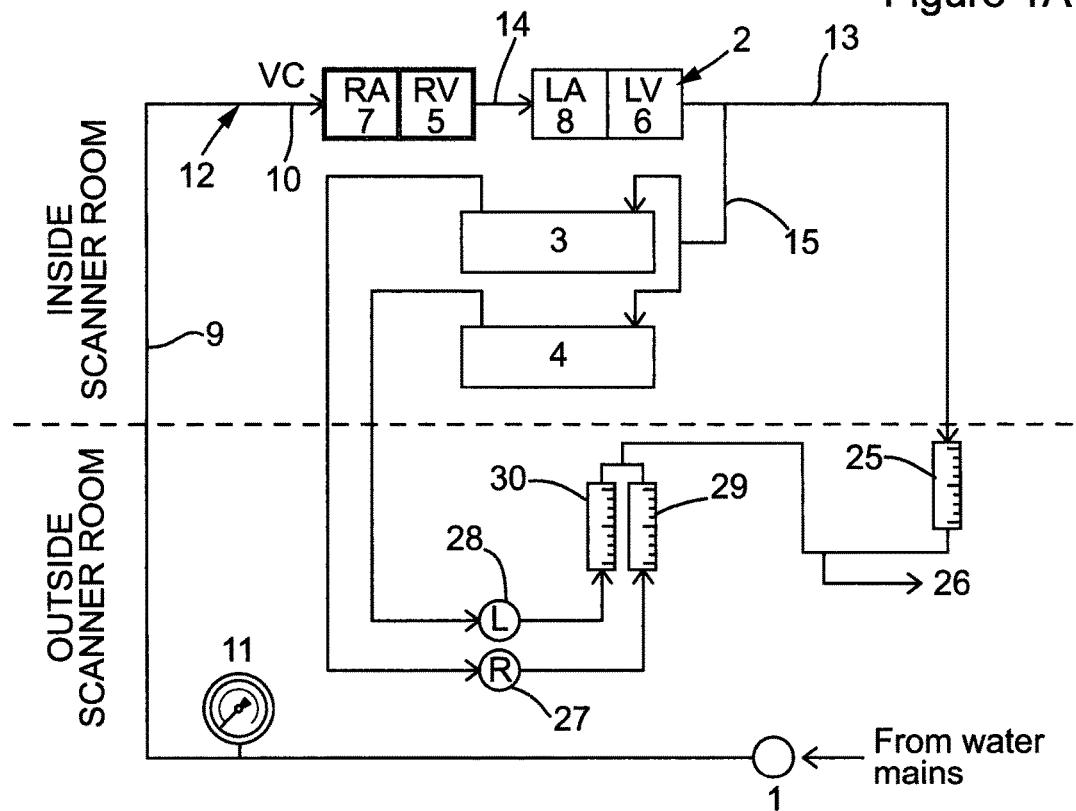
FIGS. 1A, 1B, and 1C—Schematic representation of an embodiment of the invention.
Figure 1B:
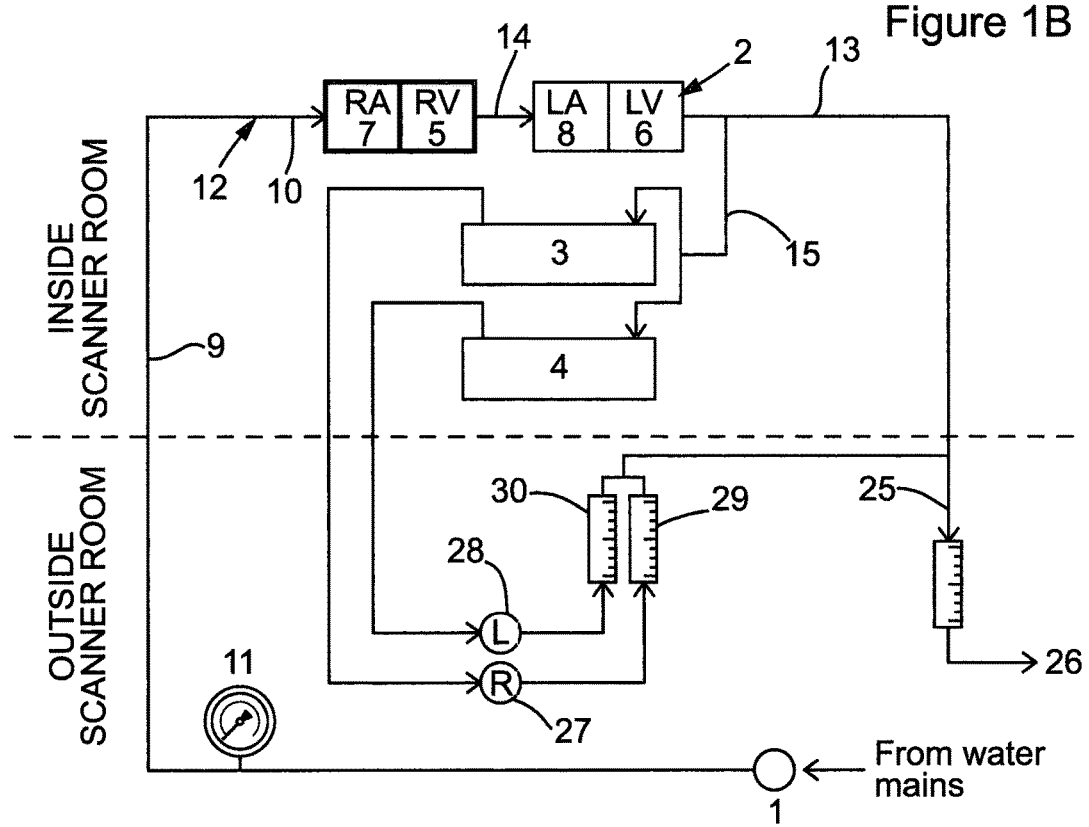

The device of FIG. 1A can be readily modified to directly measure the cardiac output (i.e. the total flow across the cardiac chambers) rather than the difference between cardiac output and absolute flow across the organs by simply changing the connections so that the outputs from both flow meters (29,30) is directed back through the vertical flow meter (25) as shown in FIG. 1B.

MR Methods

All data were acquired on a 3T Philips Achieva TX system, equipped with a 32-channel cardiac phased array receiver coil (Philips, Best, Netherlands). Perfusion data were acquired in a transverse geometry, visualizing the progression of the bolus of contrast agent in the large thoracic vessels and the myocardial compartments in the same image (FIG. 4). We used a saturation recovery gradient echo method (repetition time/echo time 3.0 ms/1.0 ms, flip angle 15°; effective k-t SENSE acceleration 3.8 fold, spatial resolution 1.2×1.2×10 mm, saturation-recovery delay 120 ms). Vector-ECG triggering was simulated at a cardiac frequency of 60 beats/minute. Data were acquired during first pass of a bolus of gadobutrol (GADOVIST®, Bayer Schering, Germany) injected at 4 mL/second followed by a 20 mL saline flush. Each bolus of gadobutrol was preceded by a diluted pre-bolus with 10% of the dose to allow quantification of myocardial blood flow, according to published methods (Christian et al., J. Magn Reson Imaging 2008:27:1271-1277, Radiology 2004:232:677-684, Ishida et al., J. Cadiovasc Magn Reson 2011:13:28). To avoid any interactions between the first and the second injection of contrast agent, a long pause was programmed on the injector to allow for a complete wash out of Gadolinium from the myocardial compartments between the first and the second injection. Several experimental protocols were used to assess the response of the system to isolated alterations of the myocardial perfusion rate, to different dosages of contrast agent or to alterations of the cardiac output. Furthermore, repeated acquisitions of SI curves in the same experimental conditions (n=6) were carried out to test the reproducibility of the SI measurements.

EXAMPLE 2

Sensitivity to Different Contrast Agent Dose

The phantom described in Example 1 was used to assess the effects of different dosages of contrast agent on the SI of the AIF and to calculate the saturation ratio (expected peak SI/observed peak SI). Gadobutrol was injected at doses representing 0.0005, 0.001, 0.0025, 0.005, 0.01 and 0.1 mmol/kg in the following experimental conditions: cardiac output 3 L/min, right and left myocardial perfusion rate 10 mL/g/min.

To assess the effects of different dosages of contrast agent on the SI of the myocardial compartments and to calculate the saturation ratio, gadobutrol was injected at doses representing 0.001, 0.0025, 0.005 and 0.01 mmol/kg in the following experimental conditions: cardiac output 3 L/min, right and left myocardial perfusion rate 10 mL/g/min.

Figure 5:
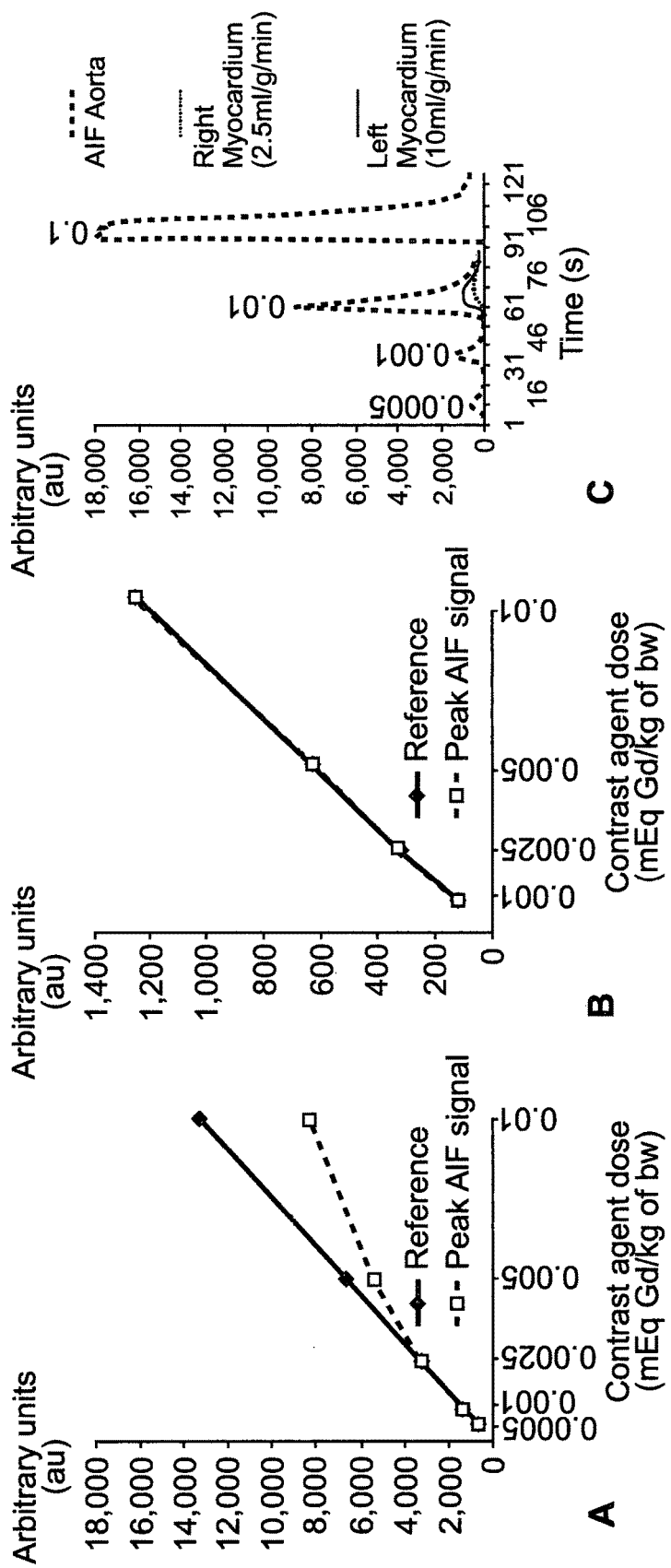
FIG. 5—Response of the system to different dosages of contrast agent.

A progressive increase in the peak AIF SI was noted with increasing doses of Gadolinium (FIG. 5, panel A). A very low dose, equivalent to 0.0005 mmol/kg of body weight, of Gadolinium gave a peak AIF intensity of 665 arbitrary units (au). An injection of 0.001 mmol/kg of body weight gave a peak AIF SI of 1335 au (versus an expected value of 1330 au), showing no saturation effects at this dosage (saturation ratio 1). An injection of 0.0025 mmol/kg of body weight gave a peak AIF SI of 3308 au (expected 3325 au), without appreciable saturation effects. At higher dosages progressive saturation effects occurred. Injections of 0.005, 0.01 and 0.1 mmol/kg of body weight gave peak values of the AIF of 5369 au (expected 6650 au), 8365 au (expected 13300 au) and 17894 (expected 133000 au), with saturation ratios of 1.24, 1.59 and 7.43, respectively. These findings show a very good agreement with human data available in the literature.

A progressive increase of SI in the myocardial compartments was also obtained in the myocardial compartments following an increase of the dosage of contrast agent administered (FIG. 5, panel B). At a dosage of 0.001 mmol/kg of body weight, the myocardial peak SI was 125 au. At dosages of 0.0025, 0.005 and 0.01 mmol/kg of body weight the myocardial peak SI was 327 au (expected 313 au), 628 au (expected 630 au) and 1245 au (expected 1260), respectively, with saturation ratio very close to 1 for all dosages.

Moreover, Fermi deconvolution quantification of myocardial blood flow gave accurate perfusion estimated across the whole range of dosages tested (gold standard perfusion rate 10 mL/g/min) of 9.7±2.1 mL/g/min, 9.9±1.3 mL/g/min and 10.1±1.2 mL/mL/min at 0.0025, 0.005 and 0.01 mmol/kg of body weight, respectively.

In order to avoid any confounding effects from signal saturation, all quantitative data presented in this manuscript were obtained by deconvolving the aortic AIF (obtained after a diluted pre-bolus of 0.001 mmol/kg of body weight) with myocardial SI curves obtained by an injection with 0.01 mmol/kg of body weight.

EXAMPLE 3

Sensitivity to Myocardial Perfusion Rate

To assess the sensitivity of the system of Example 1 to different myocardial perfusion rates, first pass perfusion measurements were performed varying the perfusion rate in the L-myoc (1, 2.5, 5, 7.5 and 10 mL/g/min), in the following experimental conditions: cardiac output 3 L/min, contrast agent dosage 0.01 mmol/kg body weight.

The system showed good sensitivity for different perfusion rates, generating independent curves for the different perfusion values tested (between 1 and 10 mL/mL/min). FIG. 6 shows the time-intensity curves recorded from the aorta and the myocardial compartments for different perfusion rates.

Quantification of myocardial perfusion, provided results consistent with the gold standard perfusion measurements obtained by the phantom's flow meters. The results were as follows (deconvolution measured perfusion rate±standard deviation/actual perfusion rate): 10.4±0.4/10, 7.4±0.3/7.5, 4.7±0.1/5, 2.9±0.2/2.5, 1.3±0.4/1 mL/g/min (p<0.0001 amongst different flow rates; n=6).

EXAMPLE 4

Sensitivity to Cardiac Output

To assess the effect of variations of the dilution of a bolus of contrast agent on the measured SI curves, the acquisition was performed for different values of cardiac output of 3 and 4 L/min, injecting 0.01 mmol/kg of Gadolinium, with right and left myocardial perfusion rate constant at 5 mL/g/min.

The system also demonstrated a good response to different cardiac output rates. At 4 L/min, the system produced a shorter and lower amplitude aortic SI curve when compared to 3 L/minute (FIG. 7). The higher dilution rate and faster washout associated with the higher cardiac output value produced a lower peak-concentration of Gadolinium in the aorta. The amplitude to the corresponding myocardial SI curves was proportional to the concentration of the contrast agent in the perfusate.

EXAMPLE 5

Reproducibility Experiments

To assess the reproducibility of the measurements, two operators repeated Examples 4 twice on different days. Moreover, reproducibility was also assessed by repeating the experiments six times under the same experimental conditions of 4 L/m of cardiac output, using 0.01 mmol/kg of Gadolinium, and a perfusion rate of 1 and 5 mL/g/min in the right and 10 mL/g/min in the left myocardial compartment. The latter experiment was repeated several times (n=6), showing excellent reproducibility between different operators and on different days both for cardiac output of 3 L/min ($R^2$ 0.999; P<0.0001) and 4 L/min ($R^2$ 0.998; P<0.0001).

Reproducibility was also demonstrated for different myocardial perfusion rates, as described in the methods. The aortic, right and left myocardial SI curves showed a very good correlation between experiments, with an adjusted $R^2$ of 0.99 and a P<0.0001 consistently.

This example demonstrates the potential of a phantom of the invention for the simulation of myocardial first-pass MR perfusion. The system allows validation of quantitative analysis versus physical measurements of flow and perfusion in different conditions of myocardial blood flow, cardiac output and contrast agent's dosage. The system is highly reproducible and therefore allows the comparison and development of novel techniques. Moreover, the presence of two independently perfused and regulated myocardial compartments allows individual alterations to be made in the myocardial blood flow of one or both. If flow is kept constant in one compartment, it can be used as a reference standard and quality control for the acquired images while modifying the perfusion rate in the other. The use of a clinical MR scanner allows testing and development of clinical protocols, with the possibility of very quick translation of novel MR methods.

New MR sequences offer the possibility of unprecedented spatial resolution and optimized infusion schemes and post-processing techniques allow true quantification of myocardial perfusion in patients. However, the development of novel MR techniques as well as post-processing methods are currently performed in preclinical studies using static phantoms, simulated data or animal experiments, or in clinical trials in volunteers and patients. The system described in this example has several advantages over the other available preclinical and clinical experimental models as discussed above.

EXAMPLE 6

Comparison of the Sensitivity of CT and MR Cardiac Perfusion Utilizing the Phantom of the Invention The phantom device of Example 1 or a modified form thereof, was used to precisely compare high-resolution k-t SENSE MR perfusion at 3 Tesla, an optimal available clinical standard, with single-phase CT perfusion under identical perfusion conditions. The comparative sensitivity of each method was evaluated with a variety of simulated perfusion deficits and CT energy levels.

In the case of the CT experiments, the polypropylene tubes (17) were replaced by modified hemodialysis filters (AV600, Frezenius SE, Bad Homburg, Germany) comprising polysulfone dialysis fibers. These were retained in situ to allow contrast diffusion while allowing separate chemical composition of a fluid in the dialysate chamber of the filter. For CT experiments the dialysate chamber was filled with 10% calcium chloride solution to enable a broad spectrum photon absorption resulting in approximately 30 Hu at 120 kV, at the lower normal range of native myocardium prior to the addition of contrast agent.

In each experiment, one myocardial compartment received unmodified flow and served as a control for the 'ischemic' myocardial compartment.

MR Acquisition Methods

MR perfusion was performed at a 3 Tesla Philips Achieva TX system equipped with a 32-channel cardiac phased array receiver coil (Philips, Best, Netherlands). A saturation recovery gradient echo method was used (repetition time/echo time 3.0 ms/1.0 ms, flip angle 15°; effective k-t SENSE acceleration 3.8 fold, spatial resolution 1.2×1.2×10 mm, saturation-recovery delay 120 msec). ECG triggering was simulated at a cardiac frequency of 60 beats/minute.

3 Tesla field strength was selected as it provides higher sensitivity than 1.5 T MRI and the high resolution k-t sequence used has been shown to provide superior image quality to standard BTFE imaging and has been selected for use in a major ongoing MRP clinical trial. 3 Tesla high spatial resolution k-t accelerated perfusion has shown excellent accuracy in comparison to invasive FFR measurement. It therefore most likely represents the optimal standard of MRP in current clinical use.

Data were acquired using first pass of a bolus of 4.5 ml gadrobutrol (GADOVIST®, Bayer, Schering, Germany) 1 mmol/ml, injected at 4 mL/second followed by a 20 mL saline flush. CT and MR injection rates and volumes were scaled in proportion with phantom size in order to replicate aortic contrast curves.

CT Methods

CT Images were acquired using a Philips iCT 256 detector CT. The perfusion phantom was elevated from the CT gantry while the CT was used in step-and-shoot mode with acquisitions every 1 second. ECG gating at 60 beats/minute was simulated using a pacing device. 100 mA tube current was used for all experiments with a 0.30 second gantry rotation time. For CT, the injection rate was 3 ml/seconds of Iodohexal 370 mg iodine (Ultravist 370) for 10 seconds, corresponding to an iodine delivery rate of 1.11 g/s.

Perfusion Image Acquisition and Analysis

Coronary blood flow to the active chamber was adjusted to 80%, 60% and 40% of the control chamber corresponding to myocardial perfusion rates of 4, 3 and 2 ml/g/min based on the perfusion volume at the imaging location. Perfusion to the control chamber was maintained at 5 ml/g/min. Comparative 100 kV and 80 kV acquisitions were also obtained with an 80% myocardial perfusion setting.

Current CTP techniques rely on analysis of contrast inflow into a region of interest (typically the descending aorta) with triggering of the perfusion scan after a short delay. As the selection of the optimal imaging time point is not possible a priori with current CT methods, both the peak and the average contrast at time points two heart beats before and after peak were evaluated to simulate clinical imaging with minor timing imperfections at various perfusion settings.

All data was analysed from recorded DICOM data with CT values recorded in Hounsfield units (Hu) and MR data in arbitrary units of signal intensity. ImageJ v1.44 (NIH, USA) and ViewForum v3.1 (Philips Healthcare, Netherlands) was used for Hounsfield and signal intensity measurements within the myocardial chamber. Time was measured from the start of signal upslope for each perfusion setting. Contrast was assessed as the difference between the signal intensity of the under-perfused and control compartment. Noise estimates for MRI and CT was ascertained from published data, with an expected segmental noise of 20.8 signal units for MRI, and noise values of 18.8, 24.6 and 40.3 for 120 kV, 100 kV and 80 kV CT respectively.

Results

The aortic contrast density input function and myocardial density functions measured in the phantom resemble clinical and physiological values for both MRI and CT (FIGS. 8A and 8B respectively). Contrast returned to baseline levels with continued flow through the phantom and no contrast was found to be retained by either the phantom or simulated myocardial compartments (3,4)(FIGS. 1A-C).

CT

Mean Hounsfield unit values and contrast between the normal and under-perfused myocardial compartments increased at lower kV values (FIG. 11). The increase in attenuation was approximately commensurate with the increase in noise with lower kV, such that the expected contrast-to-noise ratios are similar. As myocardial perfusion decreases, the contrast between the normal and under-perfused compartments increases both due to reduced contrast inflow, and also delayed contrast upslope (FIG. 10). A two second error of timing results in a 24-31% reduction of contrast between normal and under-perfused segments.

MRI

High concentrations of gadolinium may lead to saturation effects and the relationship between gadolinium concentration and the MR signal is non-linear, particularly at high concentrations as may be found within the LV cavity or aorta. Visual analysis does not demonstrate significant saturation effects with the myocardial compartment itself and myocardial perfusion curves closely resemble those of the corresponding CT perfusion studies.

CT vs MRI Contrast-to-Noise Ratios

Contrast between the perfused and under-perfused myocardial compartments and estimated contrast-to-noise are illustrated in FIG. 12. The contrast-to-noise for both MRI and CT are similar at all perfusion levels. Imperfect timing of CTP image acquisition (a two second timing error) during contrast inflow may lead to a 24-32% reduction in signal.

The measured CNR reflects the CNR within native images. However, it should be noted that the slice thickness of the MRP sequence used is 10 mm, while the CT slice thickness is 0.6 mm, with a smaller voxel volume. Although the effect of slice averaging may not be adequately assessed from the phantom data owing to the homogenous nature of the underlying material, from theoretical principles, the CNR for a 10 mm averaged CTP would be up to 4 times greater than 0.6 mm slice data. Real world data suggests an increase in CNR of 45% from thin to 5 mm slice CTP images. For the same slice thickness therefore, the CNR to CTP would be expected to be greater than that of MRP.

Despite the entirely distinct physical principles underlying CT and MR image formation and the exquisite sensitivity of proton relaxation to gadolinium-based contrast agents, this study demonstrates that the sensitivities of each perfusion modality when directly compared in the phantom device of the invention are similar. In this respect, it confirms the validity of the phantom device of the invention. The results obtainable in this device are clearly highly reproducible, irrespective of the scanning technique employed. Furthermore, it provides realistic contrast intensity functions. Thus it provides a useful means for comparing scanning techniques and for developing future scanning systems.

EXAMPLE 7

Calibration Procedure for First-Pass Quantitative Perfusion

The phantom described in Example 1 was used as the standard to calibrate quantitative perfusion measurements obtained by non-invasive imaging modalities using magnetic resonance imaging. Calibration is defined as a procedure that correlates the reading of an instrument (in this case a non-invasive imaging modality or a post-processing software for quantitative or semi-quantitative analysis) with those of a standard (in this case the phantom device) in order to assign units of perfusion measurement to imaging-derived perfusion indices and to check the instrument's accuracy.

The perfusion phantom device was used to create physiologically relevant conditions (values of perfusion rate). The accuracy of the perfusion phantom device was determined by the titration procedure described above. In brief, an imaging plane was identified within the phantom perfusion organ that corresponds to a known volume between the point in which the input function is measured (i.e. in the aorta) and the imaging plane including the phantom organ. In our experiment, this volume was set to 45 mL corresponding to a mass of 45 g of water, although any volume for example from 1 ml-10,000 ml could be used. This is the mass of 'tissue' that allows calculation of the phantom tissue perfusion rate (mL/g of tissue/minute) from the phantom tissue flow rate (mL/min).

Imaging-derived first-pass signal intensity curves were acquired for perfusion rates in the phantom organ of 2 mL/g/min, 3 mL/g/min and 4 mL/g/min. The images were analysed using ViewForum v6.3.1.2 (Philips, Best, Netherlands) modified with software made in-house which allows efficient segmentation of the images and export of the signal intensity curves for analysis.

Perfusion indices, obtained in this example by first-pass perfusion magnetic resonance, were calculated from imaging-derived signal intensity curves using a Fermi deconvolution method (Jerosh-Herold et al., Med Phys 1998:25:73-84). Both the extracted arterial input function (AIF) $c_{in}(t)$ and myocardial compartment SI curve q(t) values were entered into the deconvolution model that is based on the central volume principle (Wilke et al. Radiology 1997:204:373-384, Zierler Circ Res 1962:10:393-407):

$$q(t) = \int_0^t c_{in}(t-\tau) \cdot h(t)d\tau = F \int_0^t [c_{in}(\tau) - c_{out}(\tau)]d\tau,$$

in which F denotes perfusion flow and $c_{out}(t)$ the contrast concentrations in the venous outflow. The tissue impulse response h(t) is estimated by using a Marquardt-Levenberg nonlinear least square optimization method to fit a Fermi function with the following analytical expression:

$$h(\tau) = F \cdot \left[ \frac{1}{e^{(\tau-\tau_0-\tau_d)k}+1} \right] \theta(\tau_d).$$

In the above equation, F and k represent indices of the contrast agent influx and efflux parameters, $\theta(\tau_d)$ is the unit step function, $\tau_d$ accounts for the delay time between the appearance of signal in LV blood pool $c_{in}(t)$ and myocardial region of interest q(t) and finally $\tau_0$ characterizes the width of the shoulder of the Fermi function during which little or no contrast agent has left region of interest. This fitting procedure yielded the time curves for tissue impulse response function, h(t). The deconvolution-derived perfusion index was defined for each set of perfusion rate as the h(t=0).

In this magnetic resonance example, the AIF was obtained at the level of the aorta of the phantom according to a dual-bolus protocol, as described in Ishida et al. JCMR 2011; 13:28.

In this magnetic resonance example, the perfusion index considered for calibration is the result of the deconvolution procedure, in particular h(t=0). This is dimensionless due to its deconvolution from arbitrary units of signal intensities produced by the instrument and will be referred to in the dimensional analysis as Units of Deconvolution (U.D.).

A regression procedure was used to calculate the mathematical relationship between the imaging-derived perfusion indices and reference perfusion rates provided by the standard.

In this example, perfusion rate of 2 mL/g/min corresponded to an h(t=0) of 0.0177, 3 mL/g/min corresponded to an h(t=0) of 0.0270 and 4 mL/g/min corresponded to an h(t=0) of 0.0362.

The values produced by regression resulted in the calibration curve of $$h(t=0) = 0.00925*P + 0.0008$$

where P represents the perfusion rate in mL/g/min. This corresponds to a dimensional analysis of $$h(t=0)[U.D.] = 0.00925\left[\frac{g*min}{mL}\right][U.D.]*P\left[\frac{mL}{g*min}\right] + 0.0008[U.D.]$$

Based on this equation, the actual perfusion rate can be calculated from the imaging-derived index (in this example the deconvolution results, h(t=0)) as follows $$P = \frac{h(t=0)[U.D.] - 0.0008[U.D.]}{0.00925[U.D.]}\left[\frac{mL}{g*min}\right]$$

This can be simplified:

$$P = 108\left[\frac{mL}{g*min}\right]\left[\frac{1}{U.D.}\right]*(h(t=0)[U.D.] - 0.0008[U.D.])$$

and approximated to:

$$P = 108\left[\frac{mL}{g*min}\right]\left[\frac{1}{U.D.}\right]*h(t=0)[U.D.]$$

In this example $$108\left[\frac{mL}{g*min}\right]\left[\frac{1}{U.D.}\right]$$

is the calibration factor for the perfusion measurement and h(t=0)=0.0222 corresponds to a perfusion rate of 2.4 mL/g/min. In an another example, h(t=0)=0.0331 corresponds to a perfusion rate of 3.6 mL/g/min.

In this particular example, the perfusion index analysed was the result of the deconvolution procedure (h(t=0)) as described above. However the method is readily modified to derive different modalities, which could be derived from other indices related to tissue perfusion, such as area under the curve, upslope of the curve, normalized upslope of the curve, peak of the curves, relative peak of the curves, plateau of the curves, etc. The same procedure can also be applied to different imaging modalities (such as CT, PET, etc . . . ) All would provide useful means for calibrating an instrument.

Figure 1C:
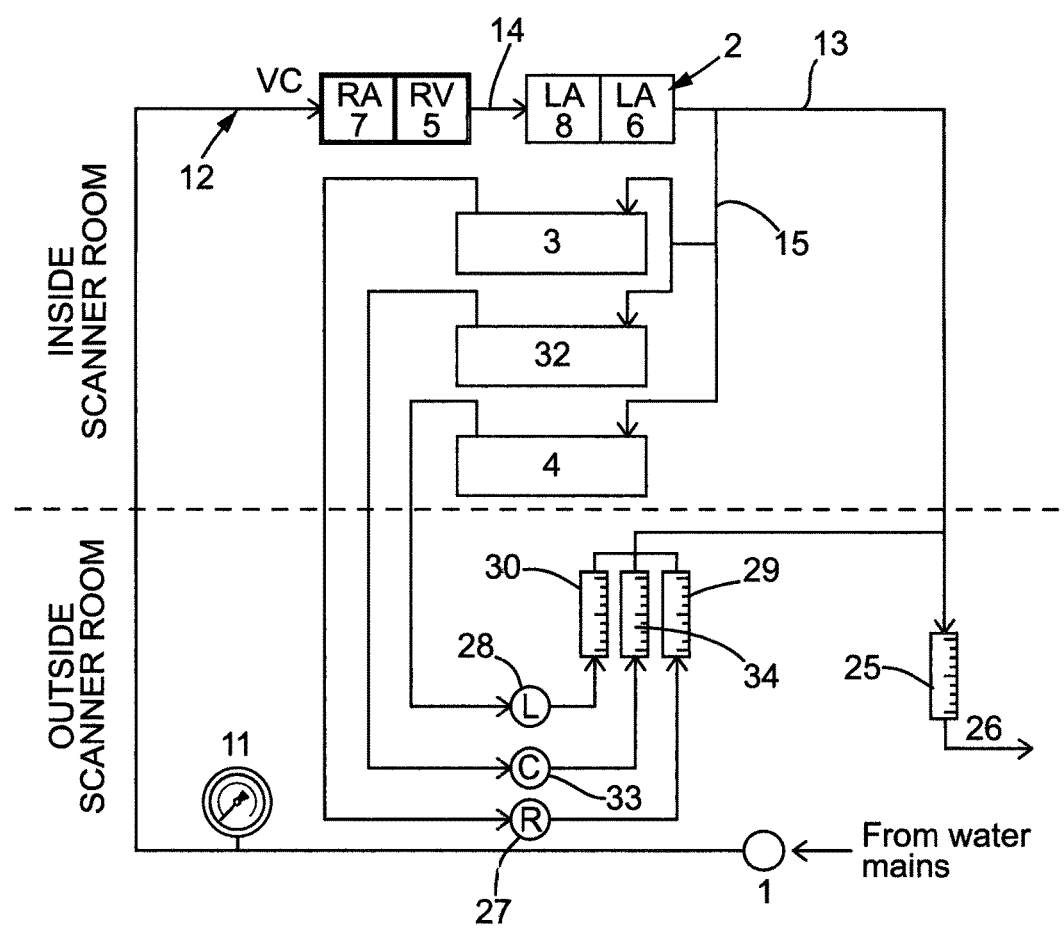
Figure 2:
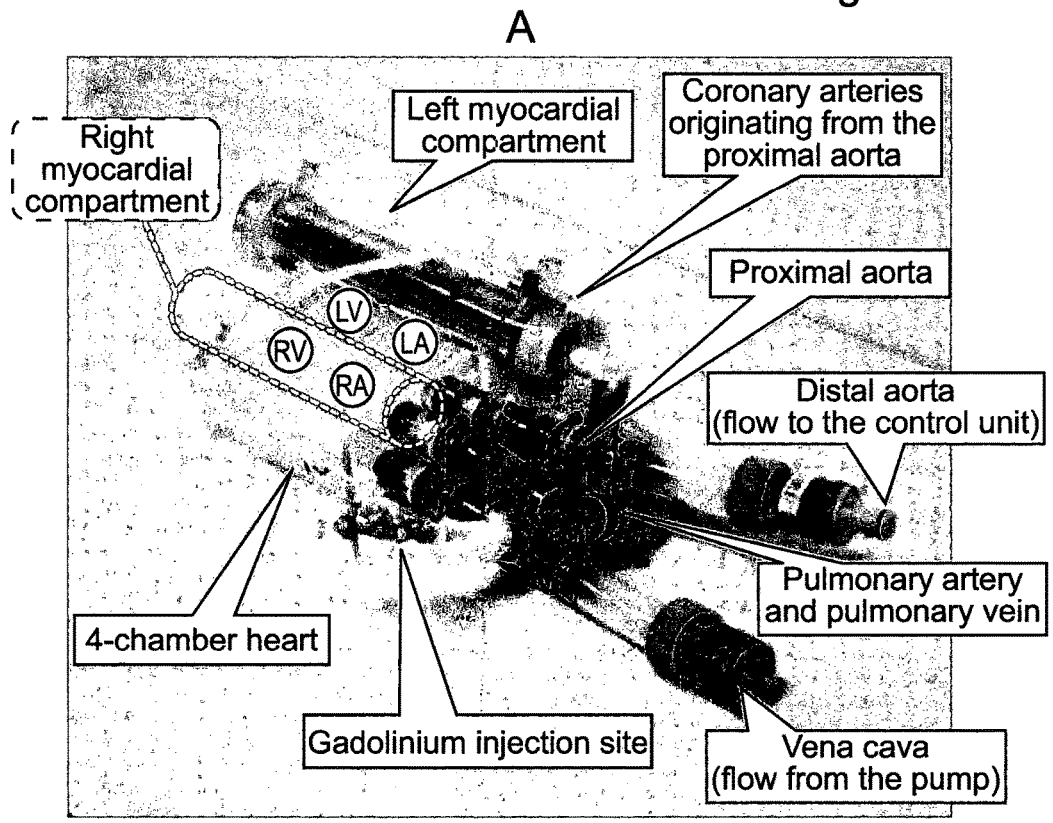
FIG. 2—(A) Picture of the perfusion phantom. The right myocardial compartment was removed and replaced with the dotted graph to allow visualization of the 4-chamber heart located below. (B) Control unit and roller pumps. The unit provides fine control of myocardial perfusion flow and precise measurement of cardiac output, maximum pressure in the circuit and myocardial perfusion. RA: right atrium; RV: right ventricle; LA: left atrium; LV: left ventricle.
Figure 2:
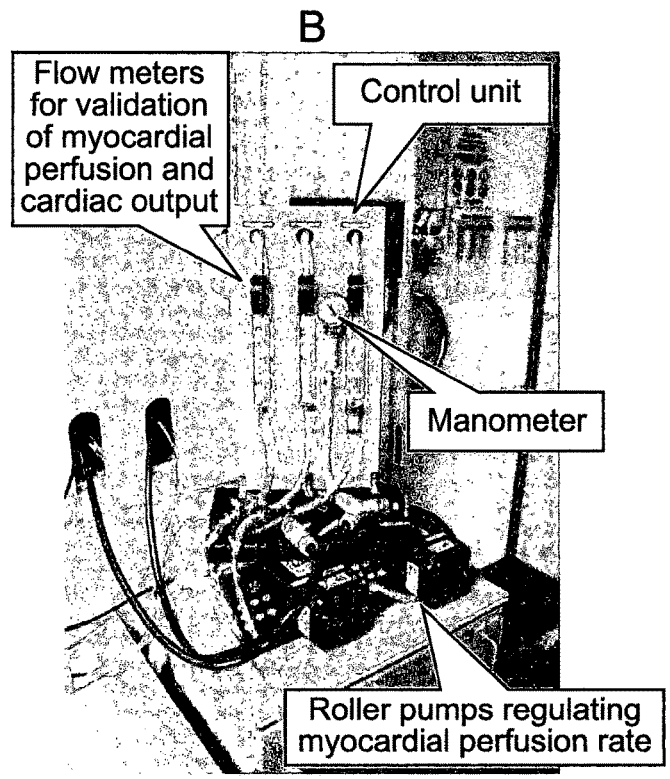

The method may also be carried out in the device illustrated in FIG. 1C in which a third central phantom organ (32) is provided. The flow through this organ (32) is controllable by means of an additional roller pump (33) located downstream of the organ (32). The volume of liquid passing through the organ (32) is measurable using a third flow meter (34). As discussed above, the provision of such a third organ provides an additional datapoint for use in a calibration procedure, and thus provides an inbuilt quality control system.

TABLE 1

Components of the perfusion phantom and their characteristics

| Section | Subsection | Size | Material |
|---------|------------|------|----------|
| Heart | Right and left atrium | 105 mL | Poly (methyl methacrylate) box |
|  | Right and left ventricle | 120 mL | Poly (methyl methacrylate) box |
| Vena cava | — | 1.6 cm diameter × 13 cm length Inner volume 26 mL | Silicone tube |
| Pulmonary artery/vein | — | 1.6 cm diameter × 44 cm length Inner volume 88 mL | Silicone tube |
| Aorta (before coronary arteries) | — | 1.6 cm diameter × 18 cm length Inner volume 36 mL | Silicone tube |
| Coronary arteries | — | 0.5 cm diameter × 30 cm length Inner volume 5.8 mL | Poly vinyl chloride (PVC) tube |

TABLE 1-continued

Components of the perfusion phantom and their characteristics

| Section | Subsection | Size | Material |
| --- | --- | --- | --- |
| Myocardium | — | 2 cm radius; 12.6 cm² section | Polypropylene (PP) tubes in a poly (methyl methacrylate) box |

The invention claimed is:

1. A phantom device for reproducing the fluid flow and perfusion in a body, said device comprising a phantom organ that may be introduced into a scanner, said phantom organ comprising a housing in which are defined a plurality of fluid channels each comprising a first end; a feed tube arranged to directly supply liquid to the first end of each of said channels and means for collecting liquid from another end of the channels, wherein at least some of said channels are of a first cross-sectional area and at least some other channels are of a reduced cross-sectional area such that a rate of fluid flow through said other channels is reduced compared to a rate of fluid flow through channels of said first cross-sectional area.

2. The phantom device of claim 1 wherein the channels of said first cross-sectional area are provided by a plurality of tubes, wherein the plurality of tubes are collected together within the housing so that the tubes are directly in contact with each other, and wherein spaces between the tubes form the said other channels of reduced cross-sectional area.

3. The phantom device of claim 2 further comprising a collection chamber for collecting liquid which has passed through the channels of reduced cross-sectional area without collecting liquid from the channels of the first cross-sectional area.

4. The phantom device of claim 1 wherein the housing comprises a liquid receiving chamber into which liquid from the feed tube is supplied, and wherein the first end of all of said channels opens into said receiving chamber.

5. The phantom device of claim 1 which further comprises a channel arranged to deliver wash liquid directly to the fluid channels.

6. The phantom device of claim 1 which comprises two phantom organs as defined in claim 1, each of which is fed by a common liquid supply, but wherein a rate of flow through each of said phantom organs is separately controllable by means of a separate control device, and wherein each control device is arranged downstream of each phantom organ.

7. The phantom device of claim 6, which comprises at least three phantom organs as defined in claim 1, each of which is fed by a common liquid supply, but wherein a rate of flow through each of said phantom organs is separately controllable by means of a separate control device, and wherein each control device is arranged downstream of each of said at least three phantom organs.

8. The phantom device of claim 1 which comprises a further element that may be introduced into a scanner, said further element comprising a phantom heart into which liquid may be supplied, a leaving tube leaving said phantom heart, wherein the feed tube for said phantom organ branches off from said leaving tube.

9. The phantom device of claim 8 wherein the phantom heart comprises a first chamber which is arranged to receive fluid from a fluid supply, a second chamber which receives fluid leaving said first chamber, a third chamber which receives fluid leaving the second chamber and a fourth chamber which receives fluid leaving said third chamber before delivering the fluid to the leaving tube.

10. The phantom device of claim 1 wherein the phantom organ is arranged to simulate a phantom myocardium, a phantom liver, a phantom kidney, a phantom muscle or a phantom brain.

11. A method for calibrating or validating a parameter of a scanner, said method comprising placing a phantom device as defined in claim 1 in a scanner so that at least an element of the device is within an imaging plane of the scanner, causing a liquid to flow through the device at a known control rate, carrying out scanning operations using the scanner and relating results obtained to a parameter of the scanner.

12. The method of claim 11 wherein the scanner is a magnetic resonance (MR) scanner, a computerized tomography (CT) scanner, a single photon emission computed tomography (SPECT) scanner, a positron emission tomography (PET) scanner, an ultrasound scanner or an X ray device.

13. A phantom device for reproducing the fluid perfusion in a body, said device comprising:
an element that may be introduced into a scanner, said element comprising a phantom heart through which fluid can flow, wherein the phantom heart comprises a first chamber which is arranged to receive fluid from a fluid supply, a second chamber which receives fluid leaving said first chamber, a third chamber which receives fluid leaving the second chamber and a fourth chamber which receives fluid leaving the third chamber;
a phantom thoracic or pulmonary system interposed between the second chamber and the third chamber; a first tube arranged to receive liquid from said fourth chamber:
a phantom organ through which fluid can flow,
a feed tube for said phantom organ, which branches off from said first tube; and
means for collecting liquid that has flowed through the device,
wherein said phantom organ comprises a housing in which are defined a plurality of fluid channels each comprising a first end; the feed tube being arranged to directly supply liquid to the first end of each of said channels and means for collecting liquid from another end of the channels, and
wherein at least some of said channels are of a first cross-sectional area and at least some other channels are of a reduced cross-sectional area such that a rate of fluid flow through said other channels is reduced compared to a rate of fluid flow through channels of said first cross-sectional area.

14. The phantom device of claim 13 wherein the first chamber, second chamber, third chamber, fourth chamber of the phantom heart, the phantom thoracic or pulmonary system, and the phantom organ, are arranged to be aligned within a single image plane of a scanner.

15. The phantom device of claim 13 wherein the first tube is modified to reproduce a pathological feature that may be present in an aorta in vivo.

16. The phantom device of claim 13, wherein means are provided to measure the flow from the phantom heart, the phantom thoracic or pulmonary system, and the phantom organ individually, to allow for a determination of the difference between simulated cardiac output and absolute flow.

17. The phantom device of claim 13, wherein means are provided to directly measure the flow from the phantom heart, the phantom thoracic or pulmonary system, and the phantom organ to allow for a determination of total simulated cardiac output.

18. The phantom device of claim 13 wherein a bubble trap is provided upstream of the device, to ensure that liquid entering the device is substantially free of gas.

19. A kit for use in conjunction with the phantom device of claim 13, said kit comprising a plurality of tube representing aortas, where at least some of the tubes are modified to simulate a pathological feature that may be present in an aorta in vivo.

20. A method for calibrating or validating a parameter of a scanner, said method comprising placing a phantom device as defined in claim 13 in a scanner so that at least an element of the device is within the imaging plane of the scanner, causing a liquid to flow through the device at a known control rate, carrying out scanning operations using the scanner and relating the results obtained to the parameter of the scanner.

21. The method of claim 20 wherein the scanner is a magnetic resonance (MR) scanner, a computerised tomography (CT) scanner, a single photon emission computed tomography (SPECT) scanner, a positron emission tomography (PET) scanner, an ultrasound scanner or an X ray device.

* * * * *